US008044055B2

(12) United States Patent
Caroff et al.

(10) Patent No.: US 8,044,055 B2
(45) Date of Patent: *Oct. 25, 2011

(54) 2-PHENYL-6-AMINOCARBONYL-PYRIMIDINE DERIVATIVES AND THEIR USE AS P2Y12 RECEPTOR

(75) Inventors: Eva Caroff, Ranspach-le-Haut (FR); Kurt Hilpert, Hofstetten (CH); Emmanuel Meyer, Aarau (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 122 days.

This patent is subject to a terminal disclaimer.

(21) Appl. No.: 12/447,039

(22) PCT Filed: Oct. 24, 2007

(86) PCT No.: PCT/IB2007/054325
§ 371 (c)(1),
(2), (4) Date: Apr. 24, 2009

(87) PCT Pub. No.: WO2008/050301
PCT Pub. Date: May 2, 2008

(65) Prior Publication Data
US 2009/0291962 A1 Nov. 26, 2009

(30) Foreign Application Priority Data
Oct. 25, 2006 (WO) .................. PCT/IB2006/053929

(51) Int. Cl.
*C07D 239/34* (2006.01)
*A61K 31/506* (2006.01)
(52) U.S. Cl. ......... 514/252.14; 514/252.18; 514/252.19; 514/252.2; 544/295
(58) Field of Classification Search .................. 544/295; 514/252.14, 252.18, 252.19, 252.2
See application file for complete search history.

(56) References Cited

U.S. PATENT DOCUMENTS
6,855,715 B1 2/2005 Liebeschuetz et al.

FOREIGN PATENT DOCUMENTS
| JP | 53073586 | 6/1978 |
| WO | WO 02/098856 | 12/2002 |
| WO | WO 2004/052366 | 6/2004 |
| WO | WO 2006/114774 | 11/2006 |
| WO | WO 2008/044217 | 4/2008 |
| WO | WO 2009/069100 A1 | 6/2009 |
| WO | WO 2009/125365 | 10/2009 |
| WO | WO 2009/125366 | 10/2009 |
| WO | WO 2010/116328 | 10/2010 |
| WO | WO 2010/122504 | 10/2010 |

OTHER PUBLICATIONS

Feokistov et al., Adenosine A2B receptors, Pharmacological Reviews, vol. 49, No. 4, pp. 381-402, 1997.*
Parlow J.J. et al. Bioorg Med Chem Lett. Aug. 15, 2009; 19, 6148-6156. Epub Sep. 10, 2009.
Gould. P. et al., "Salt Selection for Basic Drugs", Int. J. Pharm. (1986) 33, 201-217.
Parlow J.J. et al., "Piperazinyl-Glutamate-Pyridines as Potent Orally Bioavailable P2Y12 Antagonists for Inhibition of Platelet Aggregation." Bioorg. Med. Chem. Lett. (2009). doi: 10.1016/j.bmcl.2009.06.075.
Bishop et al., 3-(αR)-α((2S,5R)-4 Allyl-2,5-dimethyl-1-piperazinyl)-3-hydroxybenzyl)-*N*-alkyl-*N*-arylbenzamides, J. Med. Chem. (2003) 46, 623-633.
Sheth et al., The Influence of Azone, Propylene Glycol and Polyethylene Glycol on in vitro Skin Penetration of Trifluorothymidine, Int. J. Pharm. (1986) 28, 201-209.
Amir, J., et al., "Treatment of thrombotic thrombocytopenic purpura with antiplatelet drugs", *Blood*, vol. 42, No. 1, pp. 27-33, (1973).
Antithrombotic Trialists' Collaboration., "Collaborative meta-analysis of randomized trials of antiplatelet therapy for prevention of death, myocardial infarction, and stroke in high risk patients", *British Medical Journal*, vol. 324, pp. 71-86, (2002).
Balduini, C.L., et al., "Platelet aggregation in platelet-rich plasma and whole blood in 120 patients with myeloproliferative disorders", *Coagulation and Transfusion Medicine*, vol. 95, No. 1, pp. 82-86, (1991).
Bertrand, M.E., et al., "Randomized multicenter comparison of conventional anticoagulation versus antiplatelet therapy in unplanned elective coronary stenting: The full anticoagulation versus aspirin and ticlopidine (FANTASTIC) study", *Circulation*, vol. 1998, pp. 1597-1603, (1998).
Brighton, T.A., et al., "Antiphospholipid antibodies and thrombosis", *Bailliere's Clinical Haematology*, vol. 7, No. 3, pp. 541-557, (1994).
Caprie Steering Committee, "A randomized, blinded, trial of clopidogrel versus aspirin in patients at risk of ischaemic events (CAPRIE)", *The Lancet*, vol. 348, pp. 1329-1339, (1996).
Collins, C.E., et al., "Review article: platelets in inflammatory bowel disease—pathogenetic role and therapeutic implications", *Aliment Pharmacol Ther.*, vol. 11, pp. 237-247, (1997).
Davies, M.J., et al., "Intramyocardial platelet aggregation in patients with unstable angina suffering sudden ischemic cardiac death", *Circulation*, vol. 73, No. 3, pp. 418-427, (1986).

(Continued)

*Primary Examiner* — Deepak Rao
(74) *Attorney, Agent, or Firm* — Hoxie & Associates LLC

(57) ABSTRACT

The invention relates to 2-phenyl-6-aminocarbonyl-pyrimidine derivatives and their use as $P2Y_{12}$ receptor antagonists in the treatment and/or prevention and/or treatment of peripheral vascular, of visceral-, hepatic- and renal-vascular, of cardiovascular and of cerebrovascular diseases or conditions associated with platelet aggregation, including thrombosis in humans and other mammals. Formula (I).

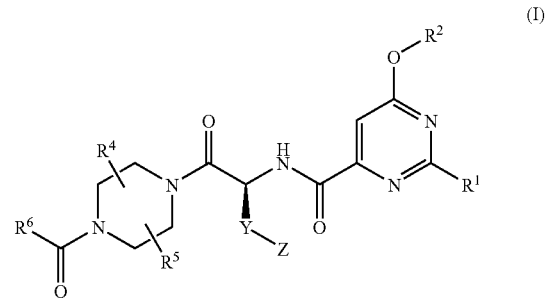

12 Claims, No Drawings

OTHER PUBLICATIONS

Felfernig-Boehm, D., et al., "Early detection of preeclampsia by determination of platelet aggregability", *Thrombosis Research*, vol. 98, pp. 139-146, (2000).

Fox, K.A.A., et al., "Benefits and risks of the combination of clopidogrel and aspirin in patients undergoing surgical revascularization for non-ST-elevation acute coronary syndrome: the clopidogrel in unstable angina to prevent recurrent ischemic events (CURE) trial", *Circulation*, vol. 110, pp. 1202-1208, (2004).

Halushka, P.V., et al., "Protective effects of aspirin in endotoxic shock", *The Journal of Pharmacology and Experimental Therapeutics*, vol. 218, pp. 464-469, (1981).

Hovens, M.M.C., et al., "Aspirin in the prevention and treatment of venous thromboembolism", *Journal of Thrombosis and Haemostasis*, vol. 4, pp. 1470-1475, (2006).

Kharbanda, R.K., et al., "Prevention of inflammation-induced endothelial dysfunction: a novel vasculo-protective action of aspirin", *Circulation*, vol. 105, pp. 2600-2604, (2002).

Megalopoulos, A., et al., "Recurrent arterial thromboses in a woman with heparin induced thrombocytopenia, successfully managed with iloprost followed by clopidogrel. An alternative therapeutic option for heparin induced thrombocytopenia type II syndrome", *International Angiology*, vol. 25, No. 1, pp. 84-89, (2006).

Mehta, S.R., et al., "Effects of pretreatment with clopidogrel and aspirin followed by long-term therapy in patients undergoing percutaneous coronary intervention: the PCI-CURE study", *The Lancet*, vol. 358, pp. 527-533, (2001).

Payne, D.A., et al., "Beneficial effects of clopidogrel combined with aspirin in reducing cerebral emboli in patients undergoing carotid endarterectomy", *Circulation*, vol. 109, pp. 1476-1481, (2004).

Stathakis, N. E., et al., "Platelet dysfunction in essential thrombocythaemia", *Annals of Clinical Research*, vol. 6, pp. 198-202, (1974).

Thorsen, C.A., et al., "The treatment of the hemolytic-uremic syndrome with inhibitors of platelet function", *The American Journal of Medicine*, vol. 66, pp. 711-716, (1979).

Triadou, P., et al., "Platelet function in sickle cell disease during steady state", *Nouvelle Revue Francaise Hematologie*, vol. 32, pp. 137-142, (1990).

University of Perugia, "Aspirin for the prevention of recurrent venous thromboembolism and cardiovascular events", Sep. 13, 2005, www.clinicaltrials.gov/ct/show/NCT00222677.

Yao, S.K., et al., "Clopidogrel is more effective than aspirin as adjuvant treatment to prevent reocclusion after thrombolysis", *Am. J. Physiol.*, vol. 267, pp. H488-H493, (1994).

* cited by examiner

2-PHENYL-6-AMINOCARBONYL-PYRIMIDINE DERIVATIVES AND THEIR USE AS P2Y12 RECEPTOR

CROSS REFERENCE TO RELATED APPLICATIONS

This application is a US filing under 35 USC 371 of PCT/IB2007/054325 filed on Oct. 24, 2007, which claims the benefit of PCT/IB2006/053929 filed on Oct. 25, 2006, the contents of each of which are incorporated herein by reference.

FIELD OF THE INVENTION

The present invention relates to 2-phenyl-6-aminocarbonyl-pyrimidine derivatives and their use as $P2Y_{12}$ receptor antagonists in the treatment and/or prevention of peripheral vascular, of visceral-, hepatic- and renal-vascular, of cardiovascular and of cerebrovascular diseases or conditions associated with platelet aggregation, including thrombosis in humans and other mammals.

BACKGROUND OF THE INVENTION

Haemostasis is referred to as the natural balance of maintaining the fluidity of the blood in the vascular system and preventing excessive blood loss subsequent to blood vessel injury by rapid formation of a solid blood clot. After vascular damage, contraction of the vessels and platelet adhesion occur immediately followed by aggregation of the platelets, activation of the coagulation cascade and finally also of the fibrinolytic system. Haemostatic abnormalities can lead to excessive bleeding or thrombosis, both life-threatening situations.

A series of antiplatelet agents have been developed over the past several years based on different mechanisms of action. The most widely used agent in antiplatelet therapy is aspirin, which irreversibly inhibits cyclooxygenase-1 and thereby affecting the thromboxane pathway. Although not optimally efficacious, treatment with aspirin remains the standard therapy against which new therapeutics are compared and judged.

Other drugs like the phosphodiesterase inhibitors dipyridamole and cilostazol, as well as the vitamin K antagonists (warfarin), are marketed but do not show all desirable features for such drugs. Three intravenously applicable, potent GPIIb/IIIa receptor antagonists (abciximab, eptifibatide, and tirofiban) blocking platelet aggregation are available on the market. Besides, some orally active GPIIb/IIIa antagonists (e.g. sibrafiban, xemilofiban or orbofiban) have not been successful in clinical development so far.

Adenosine 5'-diphosphate (ADP) is a key mediator in platelet activation and aggregation interfering with two platelet ADP receptors $P2Y_1$ and $P2Y_{12}$.

Antagonists of the platelet ADP receptor have been identified and display inhibition of platelet aggregation and antithrombotic activity. The most effective antagonists known so far are the thienopyridines ticlopidine, clopidogrel and CS-747, which have been used clinically as antithrombotic agents. It could be shown that these drugs, via their reactive metabolites, irreversibly block the ADP receptor subtype $P2Y_{12}$.

Some $P2Y_{12}$ antagonists like AR-C69931MX (Cangrelor) or AZD6140 have reached phase II clinical studies. These inhibitors are selective platelet ADP receptor antagonists, which inhibit ADP-dependent platelet aggregation, and are effective in vivo.

Piperazino-carbonylmethylaminocarbonyl-naphtyl or -quinolyl derivatives have been described as ADP receptor antagonists in WO 02/098856 and WO 2004/052366.

However, only a few 2-phenyl-4-(carbonylmethylaminocarbonyl)-pyrimidine derivatives are known in the art: indeed, only JP 53073586 describes penicillin derivatives possessing such a motif (as antibiotic agents).

DESCRIPTION OF THE INVENTION

The present invention firstly relates to the compounds of formula I

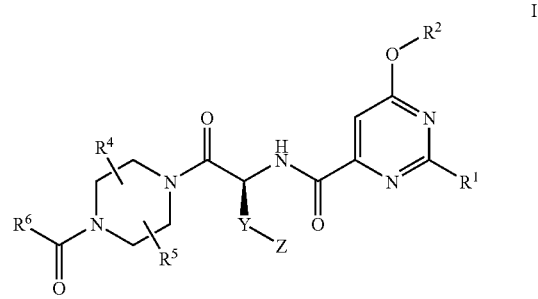

wherein
$R^1$ represents phenyl optionally substituted 1 to 3 times (preferably optionally substituted once or twice and more preferably optionally substituted once) by substituents each independently selected from the group consisting of halogen, methyl, methoxy, trifluoromethyl and trifluoromethoxy;
$R^2$ represents an alkoxyalkoxyalkyl group, a dihydroxyalkyl group, a dimethoxyalkyl group or a (2,2-dimethyl-[1,3]dioxolan-4-yl)-alkyl group;
or $R^2$ represents a group of the formula

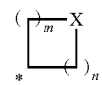

wherein
either m is 1 and n is 2 or 3, or m is 2 and n is 2; and
X represents O, S, NH, $NR^3$, SO or $SO_2$;
$R^3$ represents alkyl or arylalkyl;
or also $R^2$ represents 2,2,6,6-tetramethyl-piperidin-4-yl;
each of $R^4$ and $R^5$ represents independently hydrogen or methyl;
$R^6$ represents alkoxy; and
Y represents alkylene or phenylalkylene, and Z represents —OH, —COOH, cyano, tetrazolyl or —COOR$^7$, $R^7$ representing alkyl;
and to the salts (in particular pharmaceutically acceptable salts) of such compounds.

The compounds of formula I may contain one or more stereogenic or asymmetric centers, such as one or more asymmetric carbon atoms. The compounds of formula I may thus be present as mixtures of stereoisomers or preferably as pure stereoisomers. Mixtures of stereoisomers may be separated in a manner known to a person skilled in the art.

The compounds of formula I are $P2Y_{12}$ receptor antagonists. Accordingly, they are useful in therapy (including combination therapy), where they can be widely used as inhibitors of platelet activation, aggregation and degranulation, as promoters of platelet disaggregation or as anti-thrombotic agents.

The following paragraphs provide definitions of the various chemical moieties for the compounds according to the invention. Said definitions are intended to apply uniformly throughout the specification and claims unless an otherwise expressly set out definition provides a broader or narrower definition.

The term "halogen" refers to fluorine, chlorine, bromine or iodine, preferably to fluorine, chlorine or bromine and more preferably to fluorine.

Unless specified otherwise, the term "alkyl" (whether used alone or in combination) refers to a straight or branched chain alkyl group containing 1 to 7 carbon atoms (e.g. methyl, ethyl, propyl, iso-propyl, butyl, iso-butyl, sec-butyl, tert-butyl, n-pentyl, neopentyl, iso-pentyl, n-hexyl, iso-hexyl, n-heptyl or iso-heptyl), and more preferably 1 to 4 carbon atoms.

Unless specified otherwise, the term "alkoxy" (whether used alone or in combination) refers to a saturated straight or branched chain alkoxy group containing 1 to 6 carbon atoms (e.g. methoxy, ethoxy, propoxy, iso-propoxy, butoxy, iso-butoxy, sec-butoxy, tert-butoxy, n-pentoxy, neopentyloxy, iso-pentyloxy, n-hexyloxy or iso-hexyloxy), and preferably 1 to 4 carbon atoms.

The term "alkoxyalkoxyalkyl", as used herein, refers to a straight or branched chain alkyl group of 1 to 4 carbon atoms wherein one hydrogen atom has been replaced by a straight or branched chain alkoxy group of 1 to 3 carbon atoms, the latter being itself substituted by a straight or branched chain alkoxy group of 1 to 3 carbon atoms. Methoxyalkoxyalkyl groups (an example thereof being 2-(2-methoxy-ethoxy)-ethyl) are preferred among alkoxyalkoxyalkyl groups.

The term "dihydroxyalkyl", as used herein, refers to an alkyl group as previously defined wherein two hydrogen atoms attached to different atoms of the alkyl group have been replaced by hydroxy (i.e. —OH) groups. Examples of dihydroxyalkyl include, but are not limited to, 2,3-dihydroxy-propyl.

The term "dimethoxyalkyl", as used herein, refers to an alkyl group as previously defined wherein two hydrogen atoms attached to different atoms of the alkyl group have been replaced by methoxy (i.e. —OCH$_3$) groups. Examples of dimethoxyalkyl include, but are not limited to, 2,3-dimethoxy-propyl.

The term "(2,2-dimethyl-[1,3]dioxolan-4-yl)-alkyl" as used herein, refers to a straight or branched chain alkyl group of 1 to 4 carbon atoms wherein one hydrogen atom has been replaced by a 2,2-dimethyl-[1,3]dioxolan-4-yl group. Examples of (2,2-dimethyl-[1,3]dioxolan-4-yl)-alkyl include, but are not limited to, (R)-2,2-dimethyl-[1,3]dioxolan-4-ylmethyl and (S)-2,2-dimethyl-[1,3]dioxolan-4-ylmethyl (and in particular (R)-2,2-dimethyl-[1,3]dioxolan-4-ylmethyl).

The term "aryl" refers to an aromatic cyclic group with one, two or three rings, having from 6 to 14 carbon ring-atoms and preferably from 6 to 10 carbon ring-atoms, for example to phenyl or naphthyl groups (and notably to phenyl groups); in addition, the term "aryl" may also refer to the indanyl (e.g. indan-1-yl or indan-2-yl), tetrahydronaphtalene, biphenyl-4-yl and benzo[1,3]dioxolyl groups. Any aryl group (and in particular any phenyl group) as defined herein may be substituted with one, two or more substituents (preferably with one to three substituents, more preferably with one or two substituents and notably with one substituent), each independently selected from the group consisting of halogen, alkyl, alkoxy, hydroxymethyl, acetyl, methanesulfonyl, trifluoromethyl, trifluoromethoxy, carboxy, alkoxycarbonyl, amino, cyano and nitro. Specific examples of aryl groups are phenyl, biphenyl-4-yl, 2-fluorophenyl, 3-fluorophenyl, 4-fluorophenyl, 2-chlorophenyl, 3-chlorophenyl, 4-chlorophenyl, 2-methoxyphenyl, 3-methoxyphenyl, 4-methoxyphenyl, 2-methylphenyl, 3-methylphenyl, 4-methylphenyl, 2-trifluoromethylphenyl, 3-trifluoromethylphenyl, 4-trifluoromethylphenyl, 4-trifluoromethoxy-phenyl, 2,4-difluorophenyl, 3,4-difluorophenyl, 2,4-dimethoxyphenyl, 3-carboxyphenyl, 4-carboxyphenyl, 4-hydroxymethylphenyl, 5-amino-2,4-difluorophenyl and 2,4-dimethylphenyl.

The term "arylalkyl", as used herein, alone or in any combination, refers to an aryl group appended to the parent molecular moiety through an alkyl group wherein however the aryl group may be unsubstituted or substituted with 1 to 3 substituents selected independently from the group consisting of halogen, alkyl, alkoxy, trifluoromethyl and trifluoromethoxy. Representative examples of aralkyl include, but are not limited to, benzyl, 2-phenylethyl, 3-phenylpropyl and 2-naphth-2-ylethyl.

The term "alkylene", used alone or in combination, refers to a straight and branched divalent saturated hydrocarbon chain group with one to six carbon atoms and preferably one to four carbon atoms. Representative examples of alkylene include, but are not limited to, methylene (—CH$_2$—), ethylene (—CH$_2$—CH$_2$—), n-propylene (—CH$_2$—CH$_2$—CH$_2$—) and iso-propylene (—CH$_2$—CH(CH$_3$)—).

The term "phenylalkylene", as used herein, refers to an unsubstituted divalent phenylalkyl group wherein the alkyl is as previously defined, said divalent group being attached to the rest of the molecule by, on the one side, one of the carbon atoms of the phenyl group and by, one the other side, one of the carbon atoms of the alkyl group.

The term "phenylalkyl", as used herein, refers to an alkyl group as previously defined wherein one hydrogen atom has been replaced by an unsubstituted phenyl group. Representative examples of phenylalkyl include, but are not limited to, benzyl, 2-phenylethyl and 3-phenylpropyl.

Moreover, the sign "*" placed near an atom will be used to designate the point of attachment of a radical to the rest of a molecule. For example:

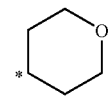

designates the tetrahydropyran-4-yl.

Besides, the following paragraphs provide definitions of various other terms. Said definitions are intended to apply uniformly throughout the specification and claims unless an otherwise expressly set out definition provides a broader or narrower definition.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively the term "around") placed before a temperature "Y" refers in the current application to an interval extending from the temperature Y minus 10° C. to Y plus 10° C., and preferably to an interval extending from Y minus 5° C. to Y plus 5° C.

The compounds of formula I will in particular be compounds of formula $I_{CE}$

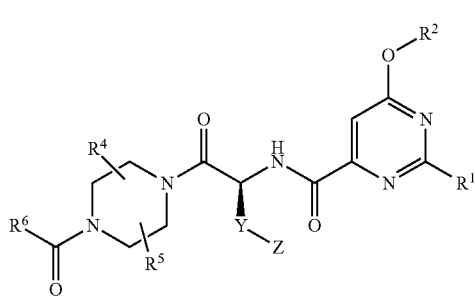

$I_{CE}$ wherein
$R^1$ represents phenyl optionally substituted once by halogen or methyl;
$R^2$ represents a methoxyalkoxyalkyl group, a dihydroxyalkyl group, a dimethoxyalkyl group or a (2,2-dimethyl-[1,3]dioxolan-4-yl)-alkyl group;
or $R^2$ represents a group of the formula

wherein
either m is 1 and n is 2 or 3, or m is 2 and n is 2; and
X represents O, S, NH or $NR^3$ (and preferably O, NH or $NR^3$);
$R^3$ represents alkyl or phenylalkyl;
or also $R^2$ represents 2,2,6,6-tetramethyl-piperidin-4-yl;
one of $R^4$ and $R^5$ represents hydrogen or methyl and the other represents hydrogen;
$R^6$ represents alkoxy; and
Y represents alkylene or phenylalkylene, and Z represents —OH, —COOH, cyano, tetrazolyl or —$COOR^7$, $R^7$ representing alkyl.

Preferred compounds of formula I will be those wherein at least one of the following characteristics is present:
  $R^1$ represents phenyl optionally substituted once or twice by substituents each independently selected from the group consisting of halogen, methyl, methoxy, trifluoromethyl and trifluoromethoxy;
  $R^2$ represents an alkoxyalkoxyalkyl group, a dihydroxyalkyl group or a (2,2-dimethyl-[1,3]dioxolan-4-yl)-alkyl group;

or $R^2$ represents a group of the formula

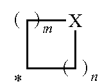

wherein
either m is 1 and n is 2 or 3, or m is 2 and n is 2; and
X represents O, S, NH or $NR^3$;
$R^3$ represents alkyl or arylalkyl;
or also $R^2$ represents 2,2,6,6-tetramethyl-piperidin-4-yl;
Y represents alkylene or phenylalkylene, and Z represents —OH, —COOH, cyano or tetrazolyl;
$R^6$ represents alkoxy of 1 to 4 carbon atoms (for example ethoxy or n-butoxy).

More preferred compounds of formula I will be those wherein at least one of the following characteristics is present:
  $R^1$ represents phenyl optionally substituted once by halogen, methyl, methoxy, trifluoromethyl and trifluoromethoxy;
  $R^2$ represents an alkoxyalkoxyalkyl group or a (2,2-dimethyl-[1,3]dioxolan-4-yl)-alkyl group;
  or $R^2$ represents a group of the formula

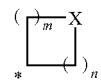

wherein
either m is 1 and n is 2 or 3, or m is 2 and n is 2; and
X represents O, NH or $NR^3$;
$R^3$ represents alkyl or phenylalkyl;
or also $R^2$ represents 2,2,6,6-tetramethyl-piperidin-4-yl;
Y represents alkylene or phenylalkylene, and Z represents —OH, —COOH or tetrazolyl (and notably —OH or —COOH);
one of $R^4$ and $R^5$ represents hydrogen or methyl and the other represents hydrogen;
$R^6$ represents alkoxy of 1 to 3 carbon atoms.

Even more preferred compounds of formula I will be those wherein at least one of the following characteristics is present:
  $R^1$ represents phenyl optionally substituted once by halogen or methyl;
  $R^2$ represents a group of the formula

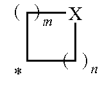

wherein
either m is 1 and n is 2 or 3, or m is 2 and n is 2; and
X represents O, NH or $NR^3$;
$R^3$ represents alkyl or phenylalkyl;
or also $R^2$ represents 2,2,6,6-tetramethyl-piperidin-4-yl;
Y represents alkylene or phenylalkylene and Z represents —COOH;
one of $R^4$ and $R^5$ represents hydrogen or methyl and the other represents hydrogen;
$R^6$ represents alkoxy of 1 to 3 carbon atoms.

Particularly preferred compounds of formula I will be those wherein at least one of the following characteristics is present:
$R^1$ represents phenyl;
$R^2$ represents a group of the formula

wherein
either m is 1 and n is 2 or 3, or m is 2 and n is 2; and
X represents O, NH or $NR^3$;
$R^3$ represents alkyl or phenylalkyl;
Y represents alkylene and Z represents —COOH;
each of $R^4$ and $R^5$ represents hydrogen;
$R^6$ represents ethoxy.

Besides, when $R^2$ represents a group of the formula

as defined in formula I, $R^2$ will preferably be selected from the group consisting of tetrahydropyran-4-yl, tetrahydrothiopyran-4-yl, 1-methyl-piperidin-3-yl, 1-benzyl-piperidin-4-yl and tetrahydrofuran-3-yl ($R^2$ being notably tetrahydropyran-4-yl, 1-methyl-piperidin-3-yl, 1-benzyl-piperidin-4-yl or tetrahydrofuran-3-yl, in particular tetrahydrofuran-3-yl).

Moreover, in a general manner, $R^6$ will preferably represent an alkoxy of 1 to 5 carbon atoms, especially an alkoxy of 2 to 4 carbon atoms. More preferably, when $R^6$ represents an alkoxy of more than 3 carbon atoms, the alkoxy chain will be linear; for example, when $R^1$ is an alkoxy of 4 carbon atoms, $R^6$ being n-butoxy will be preferred.

The following main embodiments of compounds of formula I (or of salts thereof, in particular of pharmaceutically acceptable salts thereof) are particularly preferred.

According to one main embodiment of this invention, the compounds of formula I will be such that $R^2$ represents an alkoxyalkoxyalkyl group, a dihydroxyalkyl group, a dimethoxyalkyl group or a (2,2-dimethyl-[1,3]dioxolan-4-yl)-alkyl group; such compounds will be collectively designated by "compounds of formula $I_L$" throughout the specification and claims. In such case, the compounds of formula $I_L$ will preferably be such that:
$R^1$ represents phenyl optionally substituted once or twice by substituents each independently selected from the group consisting of halogen, methyl, methoxy, trifluoromethyl and trifluoromethoxy;
$R^2$ represents an alkoxyalkoxyalkyl group, a dihydroxyalkyl group, a dimethoxyalkyl group or a (2,2-dimethyl-[1,3]dioxolan-4-yl)-alkyl group;
each of $R^4$ and $R^5$ represents independently hydrogen or methyl;
$R^6$ represents alkoxy; and
Y represents alkylene or phenylalkylene, and Z represents —OH, —COOH, cyano, tetrazolyl or —$COOR^7$, $R^7$ representing alkyl.

Preferably, the compounds of formula $I_L$ will at least have one of the following characteristics:
$R^1$ represents phenyl optionally substituted once by a substituent selected from the group consisting of halogen, methyl, methoxy, trifluoromethyl and trifluoromethoxy;
$R^2$ represents an alkoxyalkoxyalkyl group, a dihydroxyalkyl group or a (2,2-dimethyl-[1,3]dioxolan-4-yl)-alkyl group;
one of $R^4$ and $R^5$ represents hydrogen and the other represents hydrogen or methyl;
$R^6$ represents alkoxy of 1 to 4 carbon atoms;
Y represents alkylene or phenylalkylene, and Z represents —OH, —COOH, cyano or tetrazolyl (and preferably Y represents alkylene, and Z represents —OH, —COOH or tetrazolyl).

More preferably, the compounds of formula $I_L$ will at least have one of the following characteristics:
$R^1$ represents phenyl optionally substituted once by a substituent selected from the group consisting of halogen, methyl and methoxy (and notably unsubstituted phenyl);
$R^2$ represents an alkoxyalkoxyalkyl group or a (2,2-dimethyl-[1,3]dioxolan-4-yl)-alkyl group;
each of $R^4$ and $R^5$ represents hydrogen;
$R^6$ represents alkoxy of 1 to 3 carbon atoms (in particular ethoxy);
Y represents alkylene (preferably —$CH_2$—, —$CH_2$—$CH_2$— or —$CH_2$—$CH_2$—$CH_2$— and more preferably —$CH_2$—$CH_2$—) and Z represents —COOH.

According to another main embodiment of this invention, the compounds of formula I will be such that $R^2$ represents group of the formula

or such that $R^2$ represents 2,2,6,6-tetramethyl-piperidin-4-yl; such compounds will be collectively designated by "compounds of formula $I_R$" throughout the specification and claims. In such case, the compounds of formula $I_R$ will preferably be such that $R^1$ represents phenyl optionally substituted once or twice by substituents each independently selected from the group consisting of halogen, methyl, methoxy, trifluoromethyl and trifluoromethoxy.

Preferably, the compounds of formula $I_R$ will at least have one of the following characteristics:
$R^1$ represents phenyl optionally substituted once by a substituent selected from the group consisting of halogen, methyl, methoxy, trifluoromethyl and trifluoromethoxy;
$R^2$ represents a group of the formula

wherein
either m is 1 and n is 2 or 3, or m is 2 and n is 2; and
X represents O, S, NH or $NR^3$;
$R^3$ represents alkyl or arylalkyl;
or also $R^2$ represents 2,2,6,6-tetramethyl-piperidin-4-yl;
one of $R^4$ and $R^5$ represents hydrogen and the other represents hydrogen or methyl;
$R^6$ represents alkoxy of 1 to 4 carbon atoms;
Y represents alkylene or phenylalkylene, and Z represents —OH, —COOH, cyano or tetrazolyl (and preferably Y represents alkylene, and Z represents —OH or —COOH).

More preferably, the compounds of formula $I_R$ will at least have one of the following characteristics:

$R^1$ represents phenyl optionally substituted once by a substituent selected from the group consisting of halogen, methyl and methoxy (and notably unsubstituted phenyl);

$R^2$ represents a group of the formula

wherein
either m is 1 and n is 2 or 3, or m is 2 and n is 2; and
X represents O, NH or $NR^3$,
$R^3$ represents alkyl or phenylalkyl;
each of $R^4$ and $R^5$ represents hydrogen;
$R^6$ represents alkoxy of 1 to 3 carbon atoms (in particular ethoxy);
Y represents alkylene (preferably —$CH_2$—, —$CH_2$—$CH_2$— or —$CH_2$—$CH_2$—$CH_2$— and more preferably —$CH_2$—$CH_2$—) and Z represents —COOH.

The following compounds of general formula I are especially preferred:

4-[(S)-4-carboxy-2-({6-[2-(2-methoxy-ethoxy)-ethoxy]-2-phenyl-pyrimidine-4-carbonyl}-amino)-butyryl]-piperazine-1-carboxylic acid ethyl ester;

4-((S)-4-carboxy-2-{[6-((R)-2,2-dimethyl-[1,3]dioxolan-4-ylmethoxy)-2-phenyl-pyrimidine-4-carbonyl]-amino}-butyryl)-piperazine-1-carboxylic acid ethyl ester;

4-((S)-4-carboxy-2-{[6-((S)-2,3-dihydroxy-propoxy)-2-phenyl-pyrimidine-4-carbonyl]-amino}-butyryl)-piperazine-1-carboxylic acid ethyl ester;

4-((S)-4-carboxy-2-{[6-((R)-2,3-dimethoxy-propoxy)-2-phenyl-pyrimidine-4-carbonyl]-amino}-butyryl)-piperazine-1-carboxylic acid ethyl ester;

4-((S)-4-carboxy-2-{[2-phenyl-6-(tetrahydro-pyran-4-yloxy)-pyrimidine-4-carbonyl]-amino}-butyryl)-piperazine-1-carboxylic acid ethyl ester;

4-((S)-4-carboxy-2-{[6-(1-methyl-piperidin-3-yloxy)-2-phenyl-pyrimidine-4-carbonyl]-amino}-butyryl)-piperazine-1-carboxylic acid ethyl ester;

4-((S)-2-{[6-(1-benzyl-piperidin-4-yloxy)-2-phenyl-pyrimidine-4-carbonyl]-amino}-4-carboxy-butyryl)-piperazine-1-carboxylic acid ethyl ester;

4-((S)-4-carboxy-2-{[2-(4-fluoro-phenyl)-6-(tetrahydro-furan-3-yloxy)-pyrimidine-4-carbonyl]-amino}-butyryl)-piperazine-1-carboxylic acid ethyl ester;

((S)-4-carboxy-2-{[6-(tetrahydro-furan-3-yloxy)-2-p-tolyl-pyrimidine-4-carbonyl]-amino}-butyryl)-piperazine-1-carboxylic acid ethyl ester;

((S)-4-carboxy-2-{[2-phenyl-6-(tetrahydro-furan-3-yloxy)-pyrimidine-4-carbonyl]-amino}-butyryl)-3-methyl-piperazine-1-carboxylic acid ethyl ester;

4-[(S)-3-(4-carboxy-phenyl)-2-({2-phenyl-6-[(tetrahydro-furan-3-yl)oxy]-pyrimidine-4-carbonyl}-amino)-propionyl]-piperazine-1-carboxylic acid ethyl ester;

4-((S)-4-carboxy-2-{[2-phenyl-6-(piperidin-4-yloxy)-pyrimidine-4-carbonyl]-amino}-butyryl)-piperazine-1-carboxylic acid ethyl ester;

4-((S)-4-carboxy-2-{[2-phenyl-6-(2,2,6,6-tetramethyl-piperidin-4-yloxy)-pyrimidine-4-carbonyl]-amino}-butyryl)-piperazine-1-carboxylic acid ethyl ester;

4-[(S)-4-cyano-2-({2-phenyl-6-[(tetrahydro-furan-3-yl)oxy]-pyrimidine-4-carbonyl}-amino)-butyryl]-piperazine-1-carboxylic acid ethyl ester;

4-((S)-4-carboxy-2-{[2-phenyl-6-(tetrahydro-furan-3-yloxy)-pyrimidine-4-carbonyl]-amino}-butyryl)-piperazine-1-carboxylic acid ethyl ester;

4-[(S)-3-hydroxy-2-({2-phenyl-6-[(tetrahydro-furan-3-yl)oxy]-pyrimidine-4-carbonyl}-amino)-propionyl]-piperazine-1-carboxylic acid ethyl ester;

4-[(S)-2-{[2-phenyl-6-(tetrahydro-furan-3-yloxy)-pyrimidine-4-carbonyl]-amino}-4-(1H-tetrazol-5-yl)-butyryl]-piperazine-1-carboxylic acid ethyl ester;

4-((S)-4-tert-butoxycarbonyl-2-{[2-phenyl-6-(tetrahydro-pyran-4-yloxy)-pyrimidine-4-carbonyl]-amino}-butyryl)-piperazine-1-carboxylic acid ethyl ester;

4-((S)-4-tert-butoxycarbonyl-2-{[6-(1-methyl-piperidin-3-yloxy)-2-phenyl-pyrimidine-4-carbonyl]-amino}-butyryl)-piperazine-1-carboxylic acid ethyl ester;

4-((S)-2-{[6-(1-benzyl-piperidin-4-yloxy)-2-phenyl-pyrimidine-4-carbonyl]-amino}-4-tert-butoxycarbonyl-butyryl)-piperazine-1-carboxylic acid ethyl ester;

4-[(S)-3-(4-tert-butoxycarbonyl-phenyl)-2-({2-phenyl-6-[(tetrahydro-furan-3-yl)oxy]-pyrimidine-4-carbonyl}-amino)-propionyl]-piperazine-1-carboxylic acid ethyl ester;

((S)-4-tert-butoxycarbonyl-2-{[2-phenyl-6-(piperidin-4-yloxy)-pyrimidine-4-carbonyl]-amino}-butyryl)-piperazine-1-carboxylic acid ethyl ester;

4-((S)-4-tert-butoxycarbonyl-2-{[2-phenyl-6-(2,2,6,6-tetramethyl-piperidin-4-yloxy)-pyrimidine-4-carbonyl]-amino}-butyryl)-piperazine-1-carboxylic acid ethyl ester;

4-((S)-4-carboxy-2-{[6-(3-hydroxy-2-hydroxymethyl-propoxy)-2-phenyl-pyrimidine-4-carbonyl]-amino}-butyryl)-piperazine-1-carboxylic acid ethyl ester;

4-((S)-4-carboxy-2-{[2-phenyl-6-(tetrahydro-thiopyran-4-yloxy)-pyrimidine-4-carbonyl]-amino}-butyryl)-piperazine-1-carboxylic acid ethyl ester;

4-[(S)-4-carboxy-2-({2-phenyl-6-[(R)-(tetrahydro-furan-3-yl)oxy]-pyrimidine-4-carbonyl}-amino)-butyryl]-piperazine-1-carboxylic acid ethyl ester;

4-[(S)-4-carboxy-2-({2-phenyl-6-[(S)-(tetrahydro-furan-3-yl)oxy]-pyrimidine-4-carbonyl}-amino)-butyryl]-piperazine-1-carboxylic acid ethyl ester;

4-[(S)-4-carboxy-2-({2-phenyl-6-[tetrahydro-furan-3-yloxy]-pyrimidine-4-carbonyl}-amino)-butyryl]-piperazine-1-carboxylic acid ethyl ester;

4-[(S)-4-carboxy-2-({2-phenyl-6-[tetrahydro-furan-3-yloxy]-pyrimidine-4-carbonyl}-amino)-butyryl]-piperazine-1-carboxylic acid butyl ester;

4-[(S)-4-carboxy-2-({2-phenyl-6-[(S)-(tetrahydro-furan-3-yl)oxy]-pyrimidine-4-carbonyl}-amino)-butyryl]-piperazine-1-carboxylic acid butyl ester;

4-[(S)-4-carboxy-2-({2-phenyl-6-[(R)-(tetrahydro-furan-3-yl)oxy]-pyrimidine-4-carbonyl}-amino)-butyryl]-piperazine-1-carboxylic acid butyl ester;

4-((S)-4-tert-butoxycarbonyl-2-{[6-(2,2-dimethyl-[1,3]dioxan-5-ylmethoxy)-2-phenyl-pyrimidine-4-carbonyl]-amino}-butyryl)-piperazine-1-carboxylic acid ethyl ester;

4-((S)-4-tert-butoxycarbonyl-2-{[2-phenyl-6-(tetrahydro-thiopyran-4-yloxy)-pyrimidine-4-carbonyl]-amino}-butyryl)-piperazine-1-carboxylic acid ethyl ester;

4-[(S)-4-tert-butoxycarbonyl-2-({2-phenyl-6-[(S)-(tetrahydro-furan-3-yl)oxy]-pyrimidine-4-carbonyl}-amino)-butyryl]-piperazine-1-carboxylic acid ethyl ester;

4-[(S)-4-tert-butoxycarbonyl-2-({2-phenyl-6-[(S)-(tetrahydro-furan-3-yl)oxy]-pyrimidine-4-carbonyl}-amino)-butyryl]-piperazine-1-carboxylic acid butyl ester;

4-[(S)-4-tert-butoxycarbonyl-2-({2-phenyl-6-[(R)-(tetrahydro-furan-3yl)oxy]-pyrimidine-4-carbonyl}-amino)-butyryl]-piperazine-1-carboxylic acid butyl ester;

4-((S)-4-carboxy-2-{[2-phenyl-6-(piperidin-4-yloxy)-pyrimidine-4-carbonyl]-amino}-butyryl)-piperazine-1-carboxylic acid butyl ester;

4-((S)-4-tert-butoxycarbonyl-2-{[2-phenyl-6-(piperidin-4-yloxy)-pyrimidine-4-carbonyl]-amino}-butyryl)-piperazine-1-carboxylic acid butyl ester;

as well as the salts thereof (in particular the pharmaceutically acceptable salts thereof).

The following compounds of general formula I are more especially preferred:

4-[(S)-4-carboxy-2-({6-[2-(2-methoxy-ethoxy)-ethoxy]-2-phenyl-pyrimidine-4-carbonyl}-amino)-butyryl]-piperazine-1-carboxylic acid ethyl ester;

4-((S)-4-carboxy-2-{[6-((R)-2,2-dimethyl-[1,3]dioxolan-4-ylmethoxy)-2-phenyl-pyrimidine-4-carbonyl]-amino}-butyryl)-piperazine-1-carboxylic acid ethyl ester;

4-((S)-4-carboxy-2-{[6-((S)-2,3-dihydroxy-propoxy)-2-phenyl-pyrimidine-4-carbonyl]-amino}-butyryl)-piperazine-1-carboxylic acid ethyl ester;

4-((S)-4-carboxy-2-{[6-((R)-2,3-dimethoxy-propoxy)-2-phenyl-pyrimidine-4-carbonyl]-amino}-butyryl)-piperazine-1-carboxylic acid ethyl ester;

4-((S)-4-carboxy-2-{[2-phenyl-6-(tetrahydro-pyran-4-yloxy)-pyrimidine-4-carbonyl]-amino}-butyryl)-piperazine-1-carboxylic acid ethyl ester;

4-((S)-4-carboxy-2-{[6-(1-methyl-piperidin-3-yloxy)-2-phenyl-pyrimidine-4-carbonyl]-amino}-butyryl)-piperazine-1-carboxylic acid ethyl ester;

4-((S)-2-{[6-(1-benzyl-piperidin-4-yloxy)-2-phenyl-pyrimidine-4-carbonyl]-amino}-4-carboxy-butyryl)-piperazine-1-carboxylic acid ethyl ester;

4-((S)-4-carboxy-2-{[2-(4-fluoro-phenyl)-6-(tetrahydro-furan-3-yloxy)-pyrimidine-4-carbonyl]-amino}-butyryl)-piperazine-1-carboxylic acid ethyl ester;

((S)-4-carboxy-2-{[6-(tetrahydro-furan-3-yloxy)-2-p-tolyl-pyrimidine-4-carbonyl]-amino}-butyryl)-piperazine-1-carboxylic acid ethyl ester;

((S)-4-carboxy-2-{[2-phenyl-6-(tetrahydro-furan-3-yloxy)-pyrimidine-4-carbonyl]-amino}-butyryl)-3-methyl-piperazine-1-carboxylic acid ethyl ester;

4-[(S)-3-(4-carboxy-phenyl)-2-({2-phenyl-6-[(tetrahydro-furan-3-yl)oxy]-pyrimidine-4-carbonyl}-amino)-propionyl]-piperazine-1-carboxylic acid ethyl ester;

4-((S)-4-carboxy-2-{[2-phenyl-6-(piperidin-4-yloxy)-pyrimidine-4-carbonyl]-amino}-butyryl)-piperazine-1-carboxylic acid ethyl ester;

4-((S)-4-carboxy-2-{[2-phenyl-6-(2,2,6,6-tetramethyl-piperidin-4-yloxy)-pyrimidine-4-carbonyl]-amino}-butyryl)-piperazine-1-carboxylic acid ethyl ester;

4-[(S)-4-cyano-2-({2-phenyl-6-[(tetrahydro-furan-3-yl)oxy]-pyrimidine-4-carbonyl}-amino)-butyryl]-piperazine-1-carboxylic acid ethyl ester;

4-((S)-4-carboxy-2-{[2-phenyl-6-(tetrahydro-furan-3-yloxy)-pyrimidine-4-carbonyl]-amino}-butyryl)-piperazine-1-carboxylic acid ethyl ester;

4-[(S)-3-hydroxy-2-({2-phenyl-6-[(tetrahydro-furan-3-yl)oxy]-pyrimidine-4-carbonyl}-amino)-propionyl]-piperazine-1-carboxylic acid ethyl ester;

4-[(S)-2-{[2-phenyl-6-(tetrahydro-furan-3-yloxy)-pyrimidine-4-carbonyl]-amino}-4-(1H-tetrazol-5-yl)-butyryl]-piperazine-1-carboxylic acid ethyl ester;

4-((S)-4-tert-butoxycarbonyl-2-{[2-phenyl-6-(tetrahydro-pyran-4-yloxy)-pyrimidine-4-carbonyl]-amino}-butyryl)-piperazine-1-carboxylic acid ethyl ester;

4-((S)-4-tert-butoxycarbonyl-2-{[6-(1-methyl-piperidin-3-yloxy)-2-phenyl-pyrimidine-4-carbonyl]-amino}-butyryl)-piperazine-1-carboxylic acid ethyl ester;

4-((S)-2-{[6-(1-benzyl-piperidin-4-yloxy)-2-phenyl-pyrimidine-4-carbonyl]-amino}-4-tert-butoxycarbonyl-butyryl)-piperazine-1-carboxylic acid ethyl ester;

4-[(S)-3-(4-tert-butoxycarbonyl-phenyl)-2-({2-phenyl-6-[(tetrahydro-furan-3-yl)oxy]-pyrimidine-4-carbonyl}-amino)-propionyl]-piperazine-1-carboxylic acid ethyl ester;

((S)-4-tert-butoxycarbonyl-2-{[2-phenyl-6-(piperidin-4-yloxy)-pyrimidine-4-carbonyl]-amino}-butyryl)-piperazine-1-carboxylic acid ethyl ester;

4-((S)-4-tert-butoxycarbonyl-2-{[2-phenyl-6-(2,2,6,6-tetramethyl-piperidin-4-yloxy)-pyrimidine-4-carbonyl]-amino}-butyryl)-piperazine-1-carboxylic acid ethyl ester;

as well as the salts thereof (in particular the pharmaceutically acceptable salts thereof).

A further object of the invention is the compounds of formula I (or of formula $I_{CE}$) or their pharmaceutically acceptable salts as medicaments.

The compounds of formula I and their pharmaceutically acceptable salts can be used as medicaments, e.g. in the form of pharmaceutical compositions for enteral or parental administration.

The invention thus also relates to pharmaceutical compositions containing at least one compound according to this invention (notably a compound of formula I or $I_{CE}$), or a pharmaceutically acceptable salt thereof, and a pharmaceutically acceptable carrier, diluent or excipient. In particular, the invention relates to pharmaceutical compositions containing at least one compound of formula I (or of formula $I_{CE}$) and a pharmaceutically acceptable carrier, diluent or excipient.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compounds according to formula I and the pharmaceutically acceptable salt thereof may be used for the preparation of a medicament, and are suitable: for the treatment or prophylaxis of diseases including stable angina, unstable angina, myocardial infarction, embolism (including complications of atherosclerosis, notably embolic stroke), arterial thrombosis (including primary arterial thrombotic complications of atherosclerosis, notably thrombotic stroke), venous thrombosis (notably deep vein thrombosis), thrombosis secondary to vascular damage or to inflammation (including vasculitis, arteritis and glomerulonephritis), venoocclusive diseases, transient ischaemic attacks, peripheral vascular diseases, myocardial infarction with or without thrombolysis, myeloproliferative disease, thrombocythaemia, sickle cell disease, inflammatory bowel disease, thrombotic thrombocytopaenic purpura, haemolytic uraemic syndrome;

for preventing thrombotic complications of septicaemia, adult respiratory distress syndrome, anti-phospholipid syndrome, heparin-induced thrombocytopaenia and pre-eclampsia/eclampsia;

for preventing cardiovascular complications after certain surgery procedures (notably coronary revascularisation like angioplasty (PTCA), other vascular graft surgery, endarterectomy or stent placement) or after accidental trauma;

for preventing organ graft rejection.

Therefore, a particular object of this invention is the use of a compound of formula I (or of formula $I_{CE}$), or of a pharmaceutically acceptable salt thereof, for the manufacture of a medicament for the uses listed above, and for the manufacture of a medicament for the treatment of occlusive vascular disorders in general.

More generally, the invention relates to the use of a compound of formula I (or of formula $I_{CE}$), or of a pharmaceutically acceptable salt thereof, for the manufacture of a medicament for the treatment and/or prevention of occlusive vascular disorders as well as to the use of a compound of formula I (or of formula $I_{CE}$) for the manufacture of a medicament for the treatment and/or prevention of peripheral vascular, of visceral-, hepatic- and renal-vascular, of cardiovascular and of cerebrovascular diseases or conditions associated with platelet aggregation, including thrombosis in humans and other mammals.

Among the above-mentioned uses of compounds of formula I (or of formula $I_{CE}$) or of pharmaceutically acceptable salts thereof for the manufacture of medicaments, the uses for manufacturing medicaments for the treatment or prophylaxis of myocardial infarction, arterial thrombosis (notably thrombotic stroke), transient ischaemic attacks, peripheral vascular disease and stable and unstable angina will be preferred.

The invention further relates to the use of a compound of formula I (or of formula $I_{CE}$), or of a pharmaceutically acceptable salt thereof, for the preservation of blood products in vitro (e.g. the preservation of platelet concentrates), or for the prevention of occlusion in extra-corporeal blood or blood product treatment machines (such as renal dialysis machines or plasmapheresis machines).

The invention also relates to methods of treatment for said disorders, said methods comprising the administration to a patient in need thereof of an effective amount of a compound of formula I (or of formula $I_{CE}$) or of a pharmaceutically acceptable salt thereof.

The preferences indicated for the compounds of formula I of course apply mutatis mutandis to the compounds of formula $I_{CE}$, as well as to the salts and pharmaceutically acceptable salts of the compounds of formula I or of formula $I_{CE}$. The same applies to these compounds as medicaments, to pharmaceutical compositions containing these compounds as active principles or to the uses of these compounds for the manufacture of a medicament for the treatment of the diseases according to this invention.

According to the invention, the compounds of formula I (or of formula $I_{CE}$) can be prepared by the process described below.

Preparation of the Compounds of Formula I

Abbreviations:
The following abbreviations are used throughout the specification and the examples:
abs. anhydrous
Ac acetyl
aq. aqueous
CC column chromatography
conc. concentrated
DCC 1,3-dicyclohexylcarbodiimide
DCM dichloromethane
DIPEA diisopropylethylamine
DME 1,2-dimethoxyethane
DMF N,N-dimethylformamide
EA ethyl acetate
EDCI N-(3-dimethylaminopropyl)-N'-ethylcarbodiimide
Et ethyl
Hept heptane
Hex hexane
HOBT 1-hydroxybenzotriazole
HV high vacuum
MCPBA meta-chloroperbenzoic acid
Me methyl
n-BuLi n-butyl lithium
org. organic
Pd/C palladium on carbon
Ph phenyl
PyBOP benzotriazole-1-yl-oxy-tris-pyrrolidino-phosphonium hexafluorophosphate
TFA trifluoroacetic acid
THF tetrahydrofuran
TLC thin layer chromatography
RT room temperature
$t_R$ retention time
General Preparation Routes The various compounds of formula I can be prepared using the general routes summarized in Scheme 1 hereafter.

Scheme 1

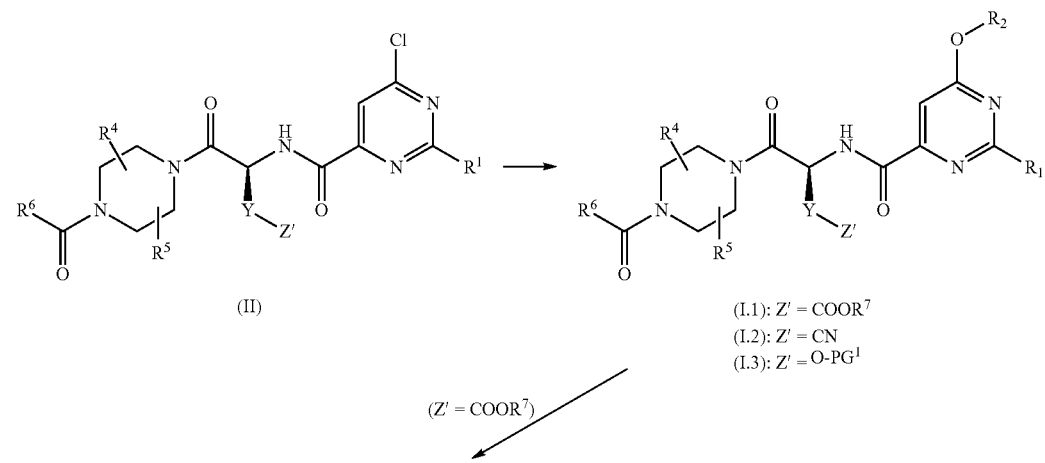

(II)

(I.1): Z' = COOR$^7$
(I.2): Z' = CN
(I.3): Z' = O-PG$^1$ (Z' = COOR$^7$)

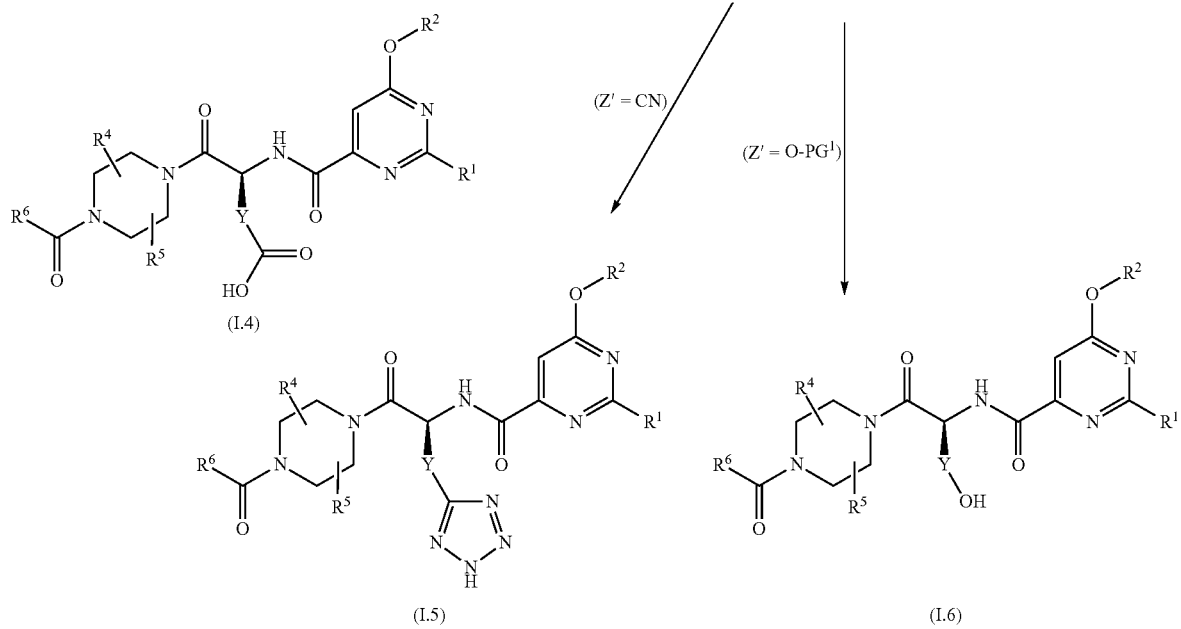

(I.4)

(I.5)

(I.6)

The compounds of formula I wherein Z represents $COOR^7$ (i.e. the compounds of general formula I.1 in which Y, $R^1$, $R^2$, $R^4$, $R^5$ and $R^6$ are as defined in formula I and Z' represents $COOR^7$), wherein Z represents CN (i.e. the compounds of general formula I.2 in which Y, $R^1$, $R^2$, $R^4$, $R^5$ and $R^6$ are as defined in formula I and Z' represents CN) or wherein Z represents O-$PG^1$, $PG^1$ being a suitable protecting group for an alcohol function (i.e. the compounds of general formula I.3 in which Y, $R^1$, $R^2$, $R^4$, $R^5$ and $R^6$ are as defined in formula I and Z' represents O-$PG^1$) can be prepared (Scheme 1) by converting a compound of formula II wherein $R^1$, $R^4$, $R^5$, $R^6$, Y and Z' have the same meanings as in formula I.1, I.2 or I.3 by aromatic substitution reaction with an alcohol of formula $HOR^2$ in the presence of a suitable base such as NaH, the reaction being carried out in a suitable solvent such as THF, MeCN or DMF and preferably at a temperature between RT and 80° C.

The compounds of formula I.4 can then be obtained (Scheme 1) by hydrolysis of the corresponding compounds of formula I.1 wherein Z' is —$COOR^7$ ($R^7$ being alkyl) under standard conditions well known to one skilled in the art.

The tetrazole derivatives of formula I.5 can be prepared (Scheme 1) by conversion of the corresponding cyano derivatives of formula I.2 wherein Z' is —CN using the well-known methodology with sodium azide, optionally in the presence of $ZnBr_2$.

The compounds of formula I.6 can be prepared (Scheme 1) by deprotection of the corresponding compounds of formula I.3 wherein Z' is —O-$PG^1$ and $PG^1$ is a suitable protecting group for an alcohol function. Suitable alcohol function protection groups and protection and deprotection methods are well known to one skilled in the art (see notably "Protective groups in organic synthesis", Greene T. W. and Wuts P. G. M., Wiley-Interscience, 1999).

Preparation of the Various Synthesis Intermediates:
Preparation of the Compounds of Formula II The compounds of formula II can be prepared (Scheme 2) by coupling the piperazine derivatives of formula III wherein Y, Z', $R^4$, $R^5$ and $R^6$ have the same meanings as in formula II with the compounds of formula IV wherein $R^1$ has the same meaning as in formula II using standard peptide coupling methods such as PyBOP, in the presence of a suitable base such as $NEt_3$, DIPEA or N-methylmorpholine and in a suitable solvent such as DCM, THF or DMF, preferably at a temperature around RT.

Scheme 2

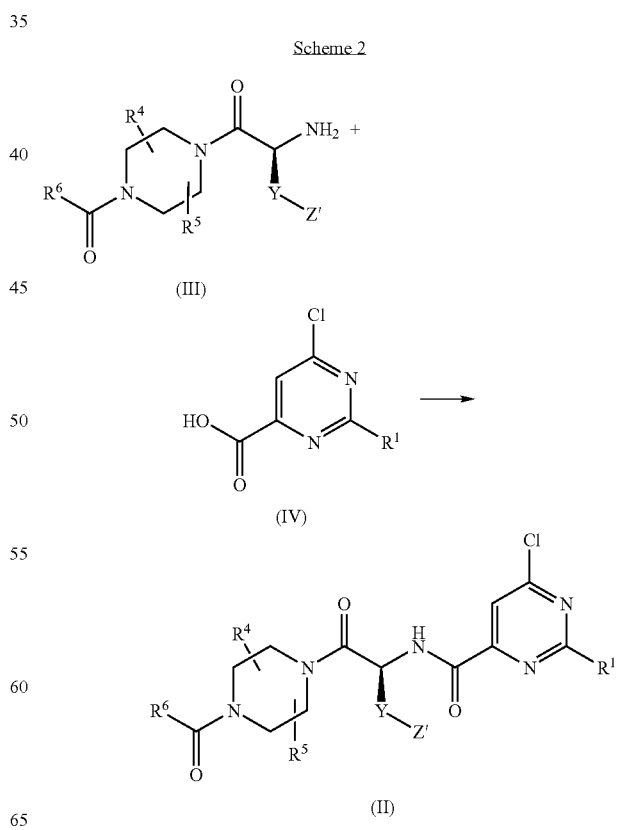

Preparation of the Compounds of Formula III

The compounds of formula III can be prepared (Scheme 3) by coupling the piperazine derivative of formula V wherein $R^4$, $R^5$ and $R^6$ have the same meanings as in formula III with a compound of formula VI wherein Y and Z' have the same meanings as in formula III, using standard peptide coupling methods such as HOBT, EDCI, DCC, PyBOP, benzotriazole-1-yl-oxy-tris-(dimethylamino)-phosphonium hexafluorophosphate, optionally in the presence of a suitable base such as $NEt_3$, DIPEA or N-methylmorpholine and in a suitable solvent such as DCM, THF or DMF, preferably at a temperature around RT. The resulting intermediates of formula VII are then deprotected using standard methods (see e.g. "Protective groups in organic synthesis", Greene T. W. and Wuts P. G. M., Wiley-Interscience, 1999) to yield the compounds of formula III.

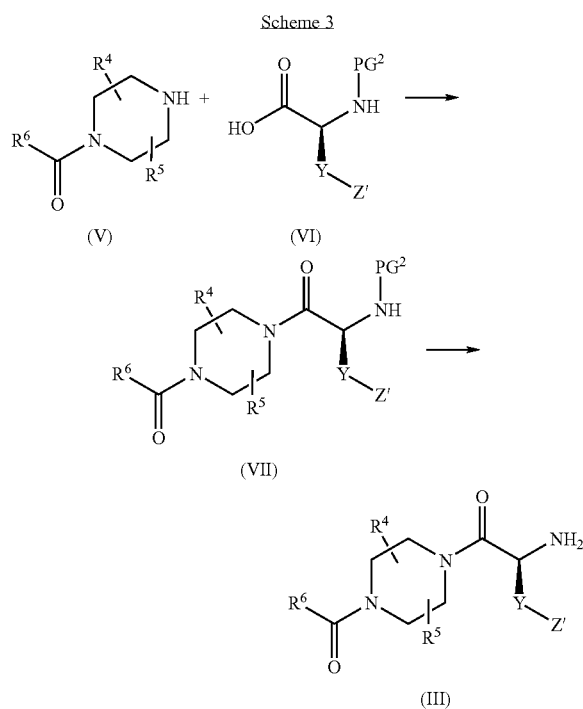

Preparation of the Compounds of Formula IV

The carboxypyrimidine derivatives of formula IV can be prepared as summarised in Scheme 4 hereafter.

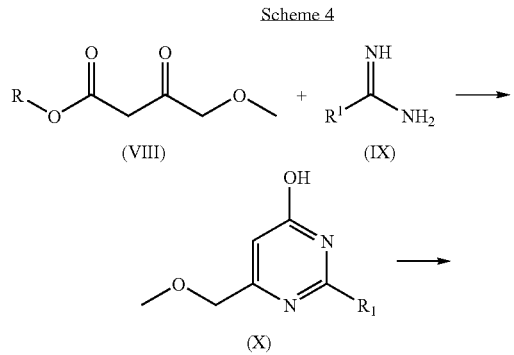

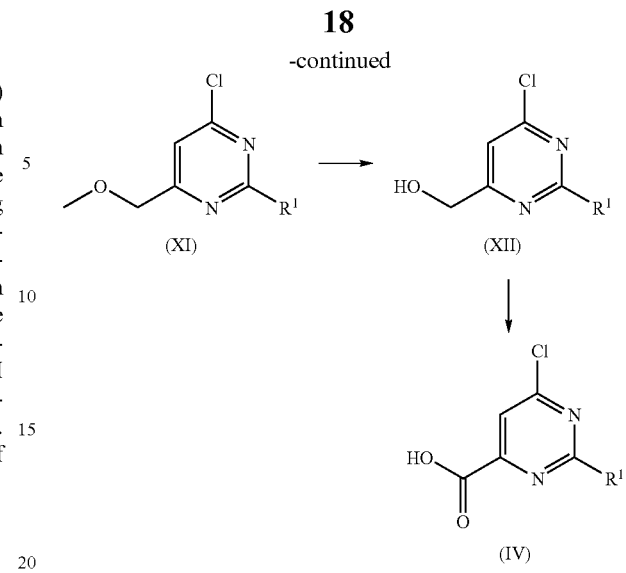

The acetoacetate derivative of formula VIII (wherein R is alkyl) is reacted with an amidine of formula IX, optionally in the presence of a suitable base such as MeONa, in a suitable solvent such as EtOH, the mixture being preferably heated at a temperature between 60 and 90° C. The compound of formula X may be chlorinated using standard conditions (e.g. phosphoryl chloride at reflux). The compound of formula XI may then be demethylated using standard reagents such as $BBr_3$, in a suitable solvent such as DCM, preferably at a temperature between −10 and 10° C.; the intermediate alcohol of formula XII thus obtained can then be oxidised, using standard oxidising agents such as $KMnO_4$, in a suitable solvent such as water, dioxane, and preferably at a temperature around RT.

Preparation of the Compounds of Formula V

Three situations have to be distinguished for the preparation of compounds of formula V, namely the case wherein $R^4$ and $R^5$ are both hydrogen (Scheme 5), the cases wherein one of $R^4$ and $R^5$ is hydrogen whereas the other is methyl (Scheme 5a) and eventually the case wherein $R^4$ and $R^5$ are both methyl.

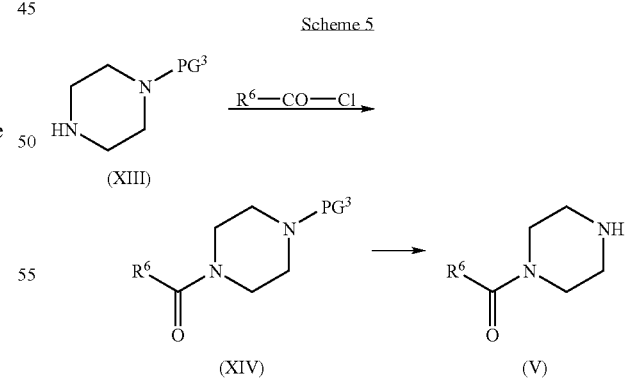

The compounds of formula V wherein $R^4$ and $R^5$ are both hydrogen can be prepared (Scheme 5) by reacting the piperazine derivative of formula XIII (wherein $PG^3$ is a suitable protecting group for an amine function) with the chloro derivative of formula $R^6$—CO—Cl (wherein $R^6$ has the same meaning as in formula V) in the presence of a suitable base such as $NEt_3$, DIPEA, N-methylmorpholine, in a suitable solvent such as DCM, THF or DMF, at a temperature preferably around RT. The intermediates of formula XIV are converted into the compounds of formula V by cleaving off the protecting group $PG^3$ using standard conditions for the deprotection of amines, and preferentially Pd/C in a suitable solvent such as MeOH, EtOH, THF or EA, or TFA or hydrochloric acid in a suitable solvent such as DCM, $Et_2O$, dioxane or EA.

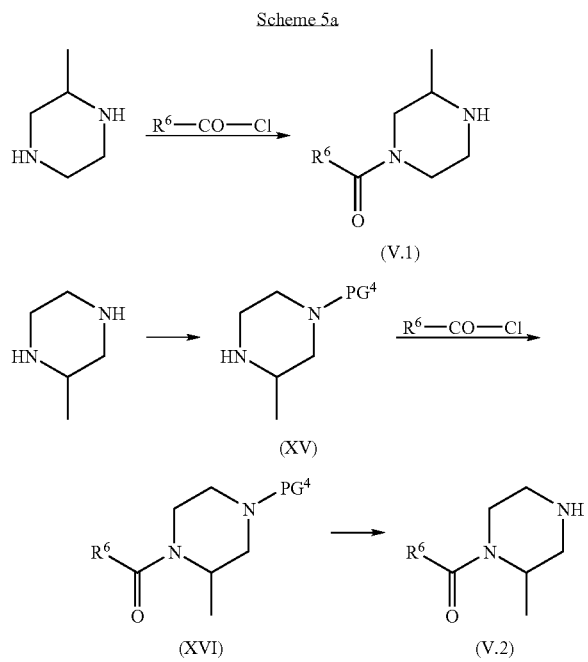

Scheme 5a

The two cases wherein one of $R^4$ and $R^5$ is hydrogen whereas the other is methyl are represented in Scheme 5a above:

The compounds of formula V.1 can be prepared (top of Scheme 5a) by direct coupling with a chloro derivative of formula $R^6$—CO—Cl.

In the case of the compounds of formula V.2 (bottom of Scheme 5a), a protection by an amine protecting group $PG^4$ is first carried out. The intermediate of formula XV thus obtained is then coupled with a chloro derivative of formula $R^6$—CO—Cl and the coupling product of formula XVI is then deprotected as described above for the compounds of formula XIV.

For the particular case wherein $R^4$ and $R^5$ are both methyl, the disubstituted piperazine may be coupled to the chloro derivative $R^6$—CO—Cl according to a procedure described by M. J. Bishop et al. in *J. Med. Chem.* (2003), 623-633, yielding the corresponding piperazine derivative of formula V.

Preparation of the Compounds of Formula VI

If not commercially available, these compounds can be prepared according to standard methods by the skilled artisan from commercially available compounds.

Particular embodiments of the invention are described in the following Examples, which serve to illustrate the invention in more detail without limiting its scope in any way.

EXAMPLES

Characterization Methods Used

The LC-MS retention times have been obtained using the following elution conditions:

A Zorbax® column (Agilent SB.Aq 5 µm, 4.6×50) was used. The two elution solvents were as follows: solvent A=water+0.05% TFA; solvent B=acetonitrile. The eluent flow rate was 4.5 ml/min and the characteristics of the eluting mixture proportion in function of the time t from start of the elution are summarized in the table below (a linear gradient being used between two consecutive time points):

| t (min) | 0 | 1 | 1.45 | 1.55 |
|---|---|---|---|---|
| Solvent A (%) | 95 | 5 | 5 | 95 |
| Solvent B (%) | 5 | 95 | 95 | 5 |

Preparative LC-MS Methods Used:

The purifications by preparative LC-MS have been performed using the conditions described hereafter.

A Zorbax® column (PrepHT SB.Aq 5 mm, 21.2×50 mm) was used. The two elution solvents were as follows: solvent A=water+0.2% formic acid; solvent B=acetonitrile+0.2% formic acid. The eluent flow rate was 95 ml/min and the characteristics of the eluting mixture proportion in function of the time t from start of the elution are summarized in the tables below (a linear gradient being used between two consecutive time points):

I) Preparative LC-MS (I):

| | t (min) | | | | | | |
|---|---|---|---|---|---|---|---|
| | 0 | 2 | 4 | 5 | 5.2 | 5.4 | 6.5 |
| Solvent A (%) | 60 | 60 | 50 | 5 | 5 | 60 | 60 |
| Solvent B (%) | 40 | 40 | 50 | 95 | 95 | 40 | 40 |

II) Preparative LC-MS (II):

| | t (min) | | | | | | |
|---|---|---|---|---|---|---|---|
| | 0 | 0.6 | 3.3 | 3.9 | 4.5 | 5.1 | 5.2 | 6 |
| Solvent A (%) | 79 | 79 | 58 | 58 | 0 | 0 | 79 | 79 |
| Solvent B (%) | 21 | 21 | 42 | 42 | 100 | 100 | 21 | 21 |

III) Preparative LC-MS (III):

| | t (min) | | | | | | |
|---|---|---|---|---|---|---|---|
| | 0 | 0.6 | 3.3 | 3.9 | 4.5 | 5.1 | 5.2 | 6 |
| Solvent A (%) | 68.5 | 68.5 | 42 | 42 | 0 | 0 | 68.5 | 68.5 |
| Solvent B (%) | 31.5 | 31.5 | 58 | 58 | 100 | 100 | 31.5 | 31.5 |

IV) Preparative LC-MS (IV):

| | | | t (min) | | | | |
|---|---|---|---|---|---|---|---|
| | 0 | 0.6 | 3.3 | 3.9 | 4.5 | 5.1 | 5.2 | 6 |
| Solvent A (%) | 58 | 58 | 31.6 | 31.6 | 0 | 0 | 58 | 58 |
| Solvent B (%) | 42 | 42 | 68.4 | 68.4 | 100 | 100 | 42 | 42 |

V) Preparative LC-MS (V):

| | | | t (min) | | | | |
|---|---|---|---|---|---|---|---|
| | 0 | 0.6 | 3.3 | 3.9 | 4.5 | 5.1 | 5.2 | 6 |
| Solvent A (%) | 42 | 42 | 21 | 21 | 0 | 0 | 42 | 42 |
| Solvent B (%) | 58 | 58 | 79 | 79 | 100 | 100 | 58 | 58 |

VI) Preparative LC-MS (VI):

| | | t (min) | | | |
|---|---|---|---|---|---|
| | 0 | 2 | 4 | 5 | 5.2 | 5.4 | 6.5 |
| Solvent A (%) | 55 | 55 | 45 | 5 | 5 | 55 | 55 |
| Solvent B (%) | 45 | 45 | 55 | 95 | 95 | 45 | 45 |

Example 1

4-[(S)-4-carboxy-2-({6-[2-(2-methoxy-ethoxy)-ethoxy]-2-phenyl-pyrimidine-4-carbonyl}-amino)-butyryl]-piperazine-1-carboxylic acid ethyl ester 1.1. 4-((S)-2-benzyloxycarbonylamino-4-tert-butoxycarbonyl-butyryl)-piperazine-1-carboxylic acid ethyl ester Z-(L)Glu(OtBu)—OH (5 g), HOBT hydrate (2.5 g) and EDCI hydrochloride (3.1 g) were dissolved in DCM/THF (1/1, 42 ml). After 15 min stirring, 1-ethoxycarbonylpiperazine (2.6 g) was added and the stirring continued overnight at RT. 150 ml of EA and 60 ml of a NaHCO₃ solution were added to the mixture and the phases were separated. The org. phase was washed with 60 ml of a 1M NaHSO₄ solution and 60 ml of a NaCl solution, dried (Na₂SO₄) and evaporated off. After HV drying, 7 g of the desired compound were obtained.
LC-MS: $t_R$=0.97 min; [M+H]⁺: 478.28.

1.2. 4-((S)-2-amino-4-tert-butoxycarbonyl-butyryl)-piperazine-1-carboxylic acid ethyl ester Intermediate 1.1 (7 g) was hydrogenated in EtOH (17 ml) with Pd/C (10%, 350 mg) for 24 h. The mixture was filtered through Celite and evaporated off. HV drying afforded 5.3 g of a colourless oil.
LC-MS: $t_R$=0.67 min; [M+H]⁺: 344.26.

1.3. 6-methoxymethyl-2-phenyl-pyrimidin-4-ol

Benzamidine (15 g), methyl-4-methoxyacetate (18.2 g) and MeONa (30% in MeOH, 23.1 ml) were dissolved in EtOH (130 ml) and the resulting mixture was refluxed overnight. It was cooled down and filtered off. The solid was washed with EtOH. The resulting ethanolic solutions were evaporated off and the residue high-vacuum dried, 27 g of a brown-yellow solid were obtained.
LC-MS: $t_R$=0.69 min; [M+H]⁺: 217.20.

1.4. 4-chloro-6-methoxymethyl-2-phenyl-pyrimidine

Phosphorous oxychloride (20 ml) was slowly added to a stirred powder of intermediate 1.3 (4.3 g). The solution was refluxed for 1 h 30, cooled down, and carefully added onto crushed ice. After 30 min stirring, the obtained suspension was extracted twice with EA. The org. layers were washed twice with a NaHCO₃ solution, dried (Na₂SO₄) and evaporated off. After HV drying, 4.17 g of the desired compound were obtained.
LC-MS: $t_R$=1.01 min; [M+H]⁺: 235.17.

1.5. (6-chloro-2-phenyl-pyrimidin-4-yl)-methanol

A solution of BBr₃ (1.83 ml) in DCM (25 ml) was syringed into a solution of intermediate 1.4 (4.17 g) in DCM (90 ml) under argon at 0° C. After 30 min at 0° C., the reaction was complete. It was quenched by the addition of Et₂O (100 ml), water (100 ml) and 1M NaOH solution (100 ml). After 1 h stirring at RT, the mixture was extracted with DCM, and the org. layers were washed with water, dried (Na₂SO₄) and evaporated. The resulting oil crushed out, and the solid obtained was washed with Hept. After HV drying, 3.29 g of a beige powder were obtained.
LC-MS: $t_R$=0.88 min; [M+H]⁺: 221.26.

1.6. 6-chloro-2-phenyl-pyrimidine-4-carboxylic acid

Intermediate 1.5 (2.2 g) was dissolved in dioxane (50 ml) and a solution of NaOH (398 mg) in water (350 ml) was added, followed by KMnO₄ (4.7 g). The mixture was stirred at RT for 2 h 30. 2M aq. HCl solution (50 ml) was added to the solution. It was stirred for 1 h and filtered off. The solution was extracted twice with EA. The org. phases were dried (Na₂SO₄) and evaporated. After HV drying, 2.24 g of a pale yellow powder were obtained.
LC-MS: $t_R$=0.88 min; [M+H]⁺: 235.24.

1.7. 4-{(S)-4-tert-butoxycarbonyl-2-[(6-chloro-2-phenyl-pyrimidine-4-carbonyl)-amino]-butyryl}-piperazine-1-carboxylic acid ethyl ester A solution of intermediate 1.6 (28.6 g) and PyBOP (70.2 g) in DCM (600 ml) was allowed to stir at RT for 10 min. A solution of intermediate 1.2 (41.9 g) in DCM (200 ml) was added to the mixture, followed by DIPEA (23 ml). The mixture was stirred for 1 h at RT. It was washed with a 1M aq. NaHSO₄ solution and with a NaHCO₃ solution. The aq. phases were back extracted with DCM, the org. layers were combined, dried (Na₂SO₄) and evaporated off. The obtained oil was dissolved in EA and the addition of Hept precipitated out some impurities. The suspension was filtered off and the filtrate was evaporated off. Column chromatography (EA/Hept 1/1) offered 44.5 g of the desired compound.
LC-MS: $t_R$=1.07 min; [M+H]⁺: 560.01.

1.8. 4-[(S)-4-carboxy-2-({6-[2-(2-methoxy-ethoxy)-ethoxy]-2-phenyl-pyrimidine-4-carbonyl}-amino)-butyryl]-piperazine-1-carboxylic acid ethyl ester A solution of 2-(2-methoxyethoxy)ethanol (0.215 ml) in DMF (3 ml) was added NaH (312 mg) and the mixture was stirred at RT for 15 min. Intermediate 1.7 (200 mg) was added and the mixture was stirred at RT until reaction completion. A NH$_4$Cl solution was added and the mixture was extracted with Et$_2$O. The aq. phase was acidified (1M HCl solution) and extracted with Et$_2$O. The org. layers were dried (Na$_2$SO$_4$) and evaporated off. Preparative TLC (DCM/MeOH/AcOH 9/1/0.1) offered 38 mg of the desired compound.

LC-MS: $t_R$=0.90 min; [M+H]$^+$: 588.66.

Example 2

4-((S)-4-carboxy-2-{[6-((R)-2,2-dimethyl-[1,3]dioxolan-4-ylmethoxy)-2-phenyl-pyrimidine-4-carbonyl]-amino}-butyryl)-piperazine-1-carboxylic acid ethyl ester This compound was prepared using a method analogous to that of Example 1, step 1.8, L-α,β-isopropyliden-glycerol replacing 2-(2-methoxyethoxy)ethanol. The title compound was however purified by preparative TLC (DCM/MeOH/AcOH 96/4/0.1), followed by preparative LC-MS (method (IV) followed by method (I)).

LC-MS: $t_R$=0.94 min; [M+H]$^+$: 600.63.

Example 3

4-((S)-4-carboxy-2-{[6-((S)-2,3-dihydroxy-propoxy)-2-phenyl-pyrimidine-4-carbonyl]-amino}-butyryl)-piperazine-1-carboxylic acid ethyl ester TFA (3 μl) was added to a solution of Example 2 (7 mg) in THF (56 μl) and water (14 μl). The mixture was stirred overnight at RT. The solvents were evaporated off and the residue was purified by preparative LC-MS (II).

LC-MS: $t_R$=0.78 min; [M+H]$^+$: 560.58.

Example 4

4-((S)-4-carboxy-2-{[6-((R)-2,3-dimethoxy-propoxy)-2-phenyl-pyrimidine-4-carbonyl]-amino}-butyryl)-piperazine-1-carboxylic acid ethyl ester 4.1. (2,3-dimethoxy-propoxymethyl)-benzene NaH (384 mg) was added to a solution of (±)-3-benzyloxy-1,2-propanediol (0.659 ml) in THF (15 ml). The mixture was stirred for 30 min at RT and iodomethane (0.606 ml) was added. The reaction mixture was stirred on at RT. MeOH was added, then water and the mixture was extracted with DCM. The org. phases were dried (Na$_2$SO$_4$) and evaporated off to afford 841 mg of the desired compound.

LC-MS: $t_R$=0.84 min; [M+H]$^+$: 211.29.

4.2. 2,3-dimethoxy-propan-1-ol

This compound was prepared using a method analogous to that of Example 1, step 1.2, intermediate 4.1 replacing intermediate 1.1.

$^1$H-NMR (CDCl$_3$): 3.70 (m, 1H); 3.60 (m, 1H); 3.46 (m, 2H); 3.43 (s, 3H); 3.38 (m, 1H); 3.33 (s, 3H).

4.3. 4-((S)-4-carboxy-2-{[6-((R)-2,3-dimethoxy-propoxy)-2-phenyl-pyrimidine-4-carbonyl]-amino}-butyryl)-piperazine-1-carboxylic acid ethyl ester This compound was prepared using a method analogous to that of Example 1, step 1.8, intermediate 4.2 replacing 2-(2-methoxyethoxy)ethanol. The title compound was however purified by preparative TLC (DCM/MeOH/AcOH 96/4/0.1), followed by preparative LC-MS (method (V) followed by method (VI)).

LC-MS: $t_R$=0.91 min; [M+H]$^+$: 588.57.

Example 5

4-((S)-4-carboxy-2-{[2-phenyl-6-(tetrahydro-pyran-4-yloxy)-pyrimidine-4-carbonyl]-amino}-butyryl)-piperazine-1-carboxylic acid ethyl ester 5.1. 4-((S)-4-tert-butoxycarbonyl-2-{[2-phenyl-6-(tetrahydro-pyran-4-yloxy)-pyrimidine-4-carbonyl]-amino}-butyryl)-piperazine-1-carboxylic acid ethyl ester To a solution of tetrahydro-2H-pyran-4-ol (0.255 ml) in THF (10 ml) was added NaH (64 mg) and the mixture was stirred at RT for 15 min. Intermediate 1.7 (300 mg) was added and the mixture was stirred at RT for 3 h. A NH$_4$Cl solution was added and the mixture was extracted with EA. The org. phases were dried (Na$_2$SO$_4$) and evaporated off to afford 600 mg of crude material, which was used without further purification.

LC-MS: $t_R$=1.08 min; [M+H]$^+$: 626.54.

5.2. 4-((S)-4-carboxy-2-{[2-phenyl-6-(tetrahydro-pyran-4-yloxy)-pyrimidine-4-carbonyl]-amino}-butyryl)-piperazine-1-carboxylic acid ethyl ester A solution of intermediate 5.1 (600 mg) in TFA/DCM (½, 15 ml) was stirred at RT for 4 h. The solvents were removed and the crude was purified by CC (DCM to DCM/MeOH 85/15) to afford 70 mg of the desired compound.

LC-MS: $t_R$=0.93 min; [M+H]$^+$: 570.43.

Example 6

4-((S)-4-carboxy-2-{[6-(1-methyl-piperidin-3-yloxy)-2-phenyl-pyrimidine-4-carbonyl]-amino}-butyryl)-piperazine-1-carboxylic acid ethyl ester trifluoroacetate salt 6.1. 4-((S)-4-tert-butoxycarbonyl-2-{[6-(1-methyl-piperidin-3-yloxy)-2-phenyl-pyrimidine-4-carbonyl]-amino}-butyryl)-piperazine-1-carboxylic acid ethyl ester This compound was prepared using a method analogous to that of Example 5, step 5.1, 3-hydroxy-1-methylpiperidine replacing tetrahydro-2H-pyran-4-ol.

LC-MS: $t_R$=0.86 min; [M+H]$^+$: 639.59.

6.2. 4-((S)-4-carboxy-2-{[6-(1-methyl-piperidin-3-yloxy)-2-phenyl-pyrimidine-4-carbonyl]-amino}-butyryl)-piperazine-1-carboxylic acid ethyl ester This compound was prepared using a method analogous to that of Example 5, step 5.2, intermediate 6.1 replacing intermediate 5.1.

LC-MS: $t_R$=0.76 min; [M+H]$^+$: 583.45.

Example 7

4-((S)-2-{[6-(1-benzyl-piperidin-4-yloxy)-2-phenyl-pyrimidine-4-carbonyl]-amino}-4-carboxy-butyryl)-piperazine-1-carboxylic acid ethyl ester trifluoroacetate salt

7.1. 4-((S)-2-{[6-(1-benzyl-piperidin-4-yloxy)-2-phenyl-pyrimidine-4-carbonyl]-amino}-4-tert-butoxycarbonyl-butyryl)-piperazine-1-carboxylic acid ethyl ester This compound was prepared using a method analogous to that of Example 5, step 5.1, N-benzyl-4-hydroxypiperidine replacing tetrahydro-2H-pyran-4-ol.
LC-MS: $t_R$=0.90 min; [M+H]$^+$: 715.54.

7.2. 4-((S)-2-{[6-(1-benzyl-piperidin-4-yloxy)-2-phenyl-pyrimidine-4-carbonyl]-amino}-4-carboxy-butyryl)-piperazine-1-carboxylic acid ethyl ester trifluoroacetate salt This compound was prepared using a method analogous to that of Example 5, step 5.2, intermediate 7.1 replacing intermediate 5.1.
LC-MS: $t_R$=0.83 min; [M+H]$^+$: 659.51.

Example 8

4-((S)-4-carboxy-2-{[2-(4-fluoro-phenyl)-6-(tetrahydro-furan-3-yloxy)-pyrimidine-4-carbonyl]-amino}-butyryl)-piperazine-1-carboxylic acid ethyl ester

8.1. 4-fluoro-benzamidine

To an ice-cold solution of hexamethyldisilazane (7 ml) in Et$_2$O (40 ml) was added n-BuLi (1.6M in hexanes, 20.6 ml), followed by a solution of 4-fluorobenzonitrile (2 g) in Et$_2$O (10 ml). After stirring at 0° C. for 10 min, the mixture was allowed to warm to RT and was stirred at RT for 20 h. The mixture was acidified to pH 1 by adding a 1M HCl solution and was washed with CHCl$_3$. The aqueous layer was then basified to pH 14 by adding Na$_2$CO$_3$ and NaOH and was extracted twice with CHCl$_3$. The org. layers were dried (Na$_2$SO$_4$) and evaporated off to afford 1.59 g of the desired compound.
LC-MS: $t_R$=0.33 min; [M+H]$^+$: 139.21.

8.2. 2-(4-fluoro-phenyl)-6-methoxymethyl-pyrimidin-4-ol

This compound was prepared using a method analogous to that of Example 1, step 1.3, intermediate 8.1 replacing benzamidine.
LC-MS: $t_R$=0.72 min; [M+H]$^+$: 235.31.

8.3. 4-chloro-6-methoxymethyl-2-(4-fluoro-phenyl)-pyrimidine

This compound was prepared using a method analogous to that of Example 1, step 1.4, intermediate 8.2 replacing intermediate 1.3.
LC-MS: $t_R$=1.04 min; [M+H]$^+$: 253.27.

8.4. [6-chloro-2-(4-fluoro-phenyl)-pyrimidin-4-yl]-methanol

This compound was prepared using a method analogous to that of Example 1, step 1.5, intermediate 8.3 replacing intermediate 1.4.
LC-MS: $t_R$=0.92 min; [M+H]$^+$: 239.25.

8.5. 6-chloro-2-(4-fluoro-phenyl)-pyrimidine-4-carboxylic acid

This compound was prepared using a method analogous to that of Example 1, step 1.6, intermediate 8.4 replacing intermediate 1.5.
LC-MS: $t_R$=0.90 min; [M+H]$^+$: 253.24.

8.6. 4-((S)-4-tert-butoxycarbonyl-2-{[6-chloro-2-(4-fluoro-phenyl)-pyrimidine-4-carbonyl]-amino}-butyryl)-piperazine-1-carboxylic acid ethyl ester This compound was prepared using a method analogous to that of Example 1, step 1.7, intermediate 8.5 replacing intermediate 1.6.
LC-MS: $t_R$=1.09 min; [M+H]$^+$: 578.41.

8.7. 4-((S)-4-carboxy-2-{[2-(4-fluoro-phenyl)-6-(tetrahydro-furan-3-yloxy)-pyrimidine-4-carbonyl]-amino}-butyryl)-piperazine-1-carboxylic acid ethyl ester This compound was prepared using a method analogous to that of Example 1, step 1.8, intermediate 8.6 replacing intermediate 1.7 and 3-hydroxytetrahydrofurane replacing 2-(2-methoxyethoxy)ethanol. The reaction mixture was however not worked up but was directly purified by preparative LC-MS (III), followed by preparative TLC (DCM/MeOH/AcOH 9/1/0.1).
LC-MS: $t_R$=0.93 min; [M+H]$^+$: 574.41.

Example 9

((S)-4-carboxy-2-{[6-(tetrahydro-furan-3-yloxy)-2-p-tolyl-pyrimidine-4-carbonyl]-amino}-butyryl)-piperazine-1-carboxylic acid ethyl ester

9.1. 6-methoxymethyl-2-p-tolyl-pyrimidin-4-ol

This compound was prepared using a method analogous to that of Example 1, step 1.3, 4-methylbenzamidine replacing benzamidine.
LC-MS: $t_R$=0.76 min; [M+H]$^+$: 231.34.

9.2. 4-chloro-6-methoxymethyl-2-p-tolyl-pyrimidine

This compound was prepared using a method analogous to that of Example 1, step 1.4, intermediate 9.1 replacing intermediate 1.3.
LC-MS: $t_R$=1.05 min; [M+H]$^+$: 249.29.

9.3. (6-chloro-2-p-tolyl-pyrimidin-4-yl)-methanol

This compound was prepared using a method analogous to that of Example 1, step 1.5, intermediate 9.2 replacing intermediate 1.4.
LC-MS: $t_R$=0.93 min; [M+H]$^+$: 235.28.

9.4. 6-chloro-2-p-tolyl-pyrimidine-4-carboxylic acid

This compound was prepared using a method analogous to that of Example 1, step 1.6, intermediate 9.3 replacing intermediate 1.5.
LC-MS: $t_R$=0.93 min; [M+H]$^+$: 249.28.

9.5. 4-{(S)-4-tert-butoxycarbonyl-2-[(6-chloro-2-p-tolyl-pyrimidine-4-carbonyl)-amino]-butyryl}-piperazine-1-carboxylic acid ethyl ester This compound was prepared using a method analogous to that of Example 1, step 1.7, intermediate 9.4 replacing intermediate 1.6.

LC-MS: $t_R$=1.11 min; [M+H]$^+$: 574.42.

9.6. ((S)-4-carboxy-2-{[6-(tetrahydro-furan-3-yloxy)-2-p-tolyl-pyrimidine-4-carbonyl]-amino}-butyryl)-piperazine-1-carboxylic acid ethyl ester This compound was prepared using a method analogous to that of Example 8, step 8.7, intermediate 9.5 replacing intermediate 8.6.

LC-MS: $t_R$=0.94 min; [M+H]$^+$: 570.44.

Example 10

((S)-4-carboxy-2-{[2-phenyl-6-(tetrahydro-furan-3-yloxy)-pyrimidine-4-carbonyl]-amino}-butyryl)-3-methyl-piperazine-1-carboxylic acid ethyl ester

10.1. 3-methyl-piperazine-1-carboxylic acid ethyl ester

To a solution of 2-methylpiperazine (1 g) in MeOH (12 ml) was added AcOH (1.8 ml). The mixture was cooled down to 0° C., ethyl chloroformate (0.95 ml) was added over a 60 min period. The mixture was allowed to warm to RT and was stirred overnight. Water was added and MeOH was evaporated off. The residue was extracted with toluene and the org. layers were washed with water. The combined aq. layers were basified to pH 14 with an aq. NaOH (2M) solution and extracted with toluene. The combined org. layers were washed with brine, dried over Na$_2$SO$_4$ and evaporated off to give 936 mg of the desired compound.

$^1$H-NMR (CDCl$_3$): 4.1 (q, 2H); 3.95 (br s, 2H); 2.9 (d, 1H); 2.75 (m, 3H); 2.4 (t, 1H); 1.6 (br s, 1H); 1.25 (t, 3H); 1.05 (t, 3H).

10.2. 4-((S)-2-benzyloxycarbonylamino-4-tert-butoxycarbonyl-butyryl)-3-methyl-piperazine-1-carboxylic acid ethyl ester This compound was prepared using a method analogous to that of Example 1, step 1.1, intermediate 10.1 replacing 1-(ethoxycarbonyl)piperazine. The compound was used in the next step without characterization.

10.3. 4-((S)-2-amino-4-tert-butoxycarbonyl-butyryl)-3-methyl-piperazine-1-carboxylic acid ethyl ester This compound was prepared using a method analogous to that of Example 1, step 1.2, intermediate 10.2 replacing intermediate 1.1.

$^1$H-NMR (CDCl$_3$): 4.66 (m, 1H); 4.08 (br s, 2H); 3.80 (br s, 2H); 3.68 (br s, 1H); 3.25 (m, 1H); 2.94 (m, 3H); 2.44 (m, 1H); 2.27 (m, 1H); 1.8 (m, 1H); 1.55 (m, 1H); 1.36 (s, 9H); 1.19 (t, 3H); 1.07 (br s, 3H).

10.4. 4-{(S)-4-tert-butoxycarbonyl-2-[(6-chloro-2-phenyl-pyrimidine-4-carbonyl)-amino]-butyryl}-3-methyl-piperazine-1-carboxylic acid ethyl ester This compound was prepared using a method analogous to that of Example 1, step 1.7, intermediate 10.3 replacing intermediate 1.2.

LC-MS: $t_R$=1.10 min; [M+H]$^+$: 574.43.

10.5. ((S)-4-carboxy-2-{[2-phenyl-6-(tetrahydro-furan-3-yloxy)-pyrimidine-4-carbonyl]-amino}-butyryl)-3-methyl-piperazine-1-carboxylic acid ethyl ester This compound was prepared using a method analogous to that of Example 8, step 8.7, intermediate 10.4 replacing intermediate 8.6.

LC-MS: $t_R$=0.93 min; [M+H]$^+$: 570.45.

Example 11

4-[(S)-3-(4-carboxy-phenyl)-2-({2-phenyl-6-[(tetrahydro-furan-3-yl)oxy]-pyrimidine-4-carbonyl}-amino)-propionyl]-piperazine-1-carboxylic acid ethyl ester

11.1. [(S)-2-benzyloxycarbonylamino-3-(4-tert-butoxycarbonyl-phenyl)-propionyl]piperazine-1-carboxylic acid ethyl ester To a solution of Z-p-carboxy-(L)Phe(OtBu)—OH (5 g) in DCM (100 ml) were added at RT HOBT (2.11 g), EDCI (2.5 g) and DIPEA (4.4 ml). After 15 min stirring at RT, 1-ethoxycarbonylpiperazine (2 g) was added and the stirring was continued at RT overnight. 150 ml of EA and 60 ml of a NaHCO$_3$ solution were added to the reaction mixture and the phases were separated. The org. phase was washed with an aq. NaHSO$_4$ (1M) solution and with brine, dried over Na$_2$SO$_4$ and evaporated off. After HV drying, 6 g of the desired compound were obtained.

LC-MS: $t_R$=1.03 min; [M+H]$^+$: 540.58.

11.2. 4-[(S)-2-amino-3-(4-tert-butoxycarbonyl-phenyl)-propionyl]-piperazine-1-carboxylic acid ethyl ester This compound was prepared using a method analogous to that of Example 1, step 1.2, intermediate 11.1 replacing intermediate 1.1.

LC-MS: $t_R$=0.75 min; [M+H]$^+$: 406.53.

11.3. 4-[(S)-2-[(4-chloro-6-phenyl-pyridine-2-carbonyl)-amino]-3-(4-ethoxycarbonyl-phenyl)-propionyl]-piperazine-1-carboxylic acid tert-butyl ester This compound was prepared using a method analogous to that of Example 1, step 1.7, intermediate 11.2 replacing intermediate 1.6. The compound was however purified twice by CC (EA/Hept. 2/1, and EA/Hept. 1/1).

LC-MS: $t_R$=1.13 min; [M+H]$^+$: 623.44.

11.4. 4-[(S)-3-(4-tert-butoxycarbonyl-phenyl)-2-({2-phenyl-6-[(tetrahydro-furan-3-yl)oxy]-pyrimidine-4-carbonyl}-amino)-propionyl]-piperazine-1-carboxylic acid ethyl ester This compound was prepared using a method analogous to that of Example 8, step 8.7, intermediate 11.3 replacing intermediate 8.6. The compound was however purified by preparative TLC (DCM/MeOH/AcOH 9.5/0.5/0.1, and EA/Hept. 1/1).
LC-MS: $t_R$=1.13 min; [M+H]$^+$: 674.70.

11.5. 4-[(S)-3-(4-carboxy-phenyl)-2-({2-phenyl-6-[(tetrahydro-furan-3-yl)oxy]-pyrimidine-4-carbonyl}-amino)-propionyl]-piperazine-1-carboxylic acid ethyl ester This compound was prepared using a method analogous to that of Example 5, step 5.2, intermediate 11.4 replacing intermediate 5.1. The compound was however not purified.
LC-MS: $t_R$=0.96 min; [M+H]$^+$: 618.65.

Example 12

4-((S)-4-carboxy-2-{[2-phenyl-6-(piperidin-4-yloxy)-pyrimidine-4-carbonyl]-amino}-butyryl)-piperazine-1-carboxylic acid ethyl ester 12.1. ((S)-4-tert-butoxycarbonyl-2-{[2-phenyl-6-(piperidin-4-yloxy)-pyrimidine-4-carbonyl]-amino}-butyryl)-piperazine-1-carboxylic acid ethyl ester This compound was prepared using a method analogous to that of Example 1, step 1.2, intermediate 7.1 replacing intermediate 1.1.
LC-MS: $t_R$=0.85 min; [M+H]$^+$: 625.54.

12.2. ((S)-4-carboxy-2-{[2-phenyl-6-(piperidin-4-yloxy)-pyrimidine-4-carbonyl]-amino}-butyryl)-piperazine-1-carboxylic acid ethyl ester This compound was prepared using a method analogous to that of Example 5, step 5.2, intermediate 12.1 replacing intermediate 5.1. The compound was however worked up by diluting the residue in EA/water and adding a Na$_2$CO$_3$ solution until pH 7. The org. layers were dried over Na$_2$SO$_4$ and evaporated off. The crude was purified by CC (DCM to DCM/MeOH 9/1).
LC-MS: $t_R$=0.74 min; [M+H]$^+$: 569.43.

Example 13

4-((S)-4-carboxy-2-{[2-phenyl-6-(2,2,6,6-tetramethyl-piperidin-4-yloxy)-pyrimidine-4-carbonyl]-amino}-butyryl)-piperazine-1-carboxylic acid ethyl ester 13.1. 4-((S)-4-tert-butoxycarbonyl-2-{[2-phenyl-6-(2,2,6,6-tetramethyl-piperidin-4-yloxy)-pyrimidine-4-carbonyl]-amino}-butyryl)-piperazine-1-carboxylic acid ethyl ester This compound was prepared using a method analogous to that of Example 5, step 5.1, 4-hydroxy-2,2,6,6-tetramethylpiperidine replacing tetrahydro-2H-pyran-4-ol. The compound was however purified by CC (DCM/MeOH 9/1).
LC-MS: $t_R$=0.90 min; [M+H]$^+$: 686.60.

13.2. 4-((S)-4-carboxy-2-{[2-phenyl-6-(2, 2,6,6-tetramethyl-piperidin-4-yloxy)-pyrimidine-4-carbonyl]-amino}-butyryl)-piperazine-1-carboxylic acid ethyl ester This compound was prepared using a method analogous to that of Example 5, step 5.2, intermediate 13.1 replacing intermediate 5.1.
LC-MS: $t_R$=0.79 min; [M+H]$^+$: 625.52.

Example 14

4-[(S)-4-cyano-2-({2-phenyl-6-[(tetrahydro-furan-3-yl)oxy]-pyrimidine-4-carbonyl}-amino)-butyryl]-piperazine-1-carboxylic acid ethyl ester 14.1. 4-((S)-2-benzyloxycarbonylamino-4-carbamoyl-butyryl)-piperazine-1-carboxylic acid ethyl ester This compound was prepared using a method analogous to that of Example 1, step 1.1, Z-(L)-Gln-OH replacing Z-(L)-Glu(OtBu)—OH.
LC-MS: $t_R$=0.74 min; [M+H]$^+$: 421.50.

14.2. 4-((S)-2-benzyloxycarbonylamino-4-cyano-butyryl)-piperazine-1-carboxylic acid ethyl ester Benzenesulfonyl chloride (19 g) was added to a solution of intermediate 14.1 (37.4 g) in dry pyridine (29.5 ml). The mixture was heated at 50° C. for 1 h, and neutralized (pH 7) by adding a 2M HCl solution. The mixture was extracted three times with EA. The combined org. phases were washed with a 1M HCl solution, a NaHCO$_3$ solution and with water, dried over Na$_2$SO$_4$ and evaporated to afford 30 g of the desired compound.
LC-MS: $t_R$=0.85 min; [M+H]$^+$: 403.48.

14.3. 4-((S)-2-amino-4-cyano-butyryl)-piperazine-1-carboxylic acid ethyl ester

This compound was prepared using a method analogous to that of Example 1, step 1.2, intermediate 14.2 replacing intermediate 1.1.
LC-MS: $t_R$=0.74 min; [M+H]$^+$: 421.50.

14.4. 4-{(S)-2-[(6-chloro-2-phenyl-pyrimidine-4-carbonyl)-amino]-4-cyano-butyryl}-piperazine-1-carboxylic acid ethyl ester This compound was prepared using a method analogous to that of Example 1, step 1.7, intermediate 14.3 replacing intermediate 1.2.
LC-MS: $t_R$=0.99 min; [M+H]$^+$: 485.33.

14.5. 4-[(S)-4-cyano-2-({2-phenyl-6-[(S)-(tetrahydro-furan-3-yl)oxy]-pyrimidine-4-carbonyl}-amino)-butyryl]-piperazine-1-carboxylic acid ethyl ester This compound was prepared using a method analogous to that of Example 8, step 8.7, intermediate 14.4 replacing intermediate 8.6. The compound was however purified by CC (EA/Hept. 0/1 to EA/Hept. 1/0).
LC-MS: $t_R$=0.97 min; [M+H]$^+$: 537.38.

Example 15

4-((S)-4-carboxy-2-{[2-phenyl-6-(tetrahydro-furan-3-yloxy)-pyrimidine-4-carbonyl]-amino}-butyryl)-piperazine-1-carboxylic acid ethyl ester This compound was prepared using a method analogous to that of Example 8, step 8.7, intermediate 1.7 replacing intermediate 8.6. The compound was however purified by CC (DCM/MeOH/AcOH 95/5/0.1).
LC-MS: $t_R$=0.92 min; [M+H]$^+$: 556.67.

Example 16

4-[(S)-3-hydroxy-2-({2-phenyl-6-[(tetrahydro-furan-3-yl)oxy]-pyrimidine-4-carbonyl}-amino)-propionyl]-piperazine-1-carboxylic acid ethyl ester

16.1. 4-((S)-3-benzyloxy-2-tert-butoxycarbonylamino-propionyl)-piperazine-1-carboxylic acid ethyl ester This compound was prepared using a method analogous to that of Example 1, step 1.1, Boc-O-benzyl-(L)-Serine replacing Z-(L)Glu(OtBu)—OH.
LC-MS: $t_R$=0.96 min; [M+H]$^+$: 436.55.

16.2. 4-((S)-2-amino-3-benzyloxy-propionyl)-piperazine-1-carboxylic acid ethyl ester hydrochloride Intermediate 16.1 (2.5 g) was dissolved in a 3 M HCl solution in EA (15 ml) and the mixture was stirred for 3 h at RT. The solvent was removed and the crude (2.68 g) was used in the next step without purification.
LC-MS: $t_R$=0.68 min; [M+H]$^+$: 336.45.

16.3. 4-{(S)-3-benzyloxy-2-[(6-chloro-2-phenyl-pyrimidine-4-carbonyl)-amino]-propionyl}-piperazine-1-carboxylic acid ethyl ester This compound was prepared using a method analogous to that of Example 1, step 1.7, intermediate 16.2 replacing intermediate 1.2. The compound was however purified by CC (EA/Hept. 2/1).
LC-MS: $t_R$=1.09 min; [M+H]$^+$: 552.35.

16.4. 4-((S)-3-benzyloxy-2-{[2-phenyl-6-(tetrahydro-furan-3-yloxy)-pyrimidine-4-carbonyl]-amino}-propionyl)-piperazine-1-carboxylic acid ethyl ester This compound was prepared using a method analogous to that of Example 8, step 8.7, intermediate 16.3 replacing intermediate 8.6. The compound was however purified by preparative LC-MS (IV).
LC-MS: $t_R$=1.07 min; [M+H]$^+$: 604.63.

16.5. 4-[(S)-3-hydroxy-2-({2-phenyl-6-[(R)-(tetrahydro-furan-3-yl)oxy]-pyrimidine-4-carbonyl}-amino)-propionyl]-piperazine-1-carboxylic acid ethyl ester This compound was prepared using a method analogous to that of Example 1, step 1.2, intermediate 16.4 replacing intermediate 1.1. The compound was however purified by preparative LC-MS (III).
LC-MS: $t_R$=0.90 min; [M+H]$^+$: 514.58.

Example 17

4-[(S)-2-{[2-phenyl-6-(tetrahydro-furan-3-yloxy)-pyrimidine-4-carbonyl]-amino}-4-(1H-tetrazol-5-yl)-butyryl]-piperazine-1-carboxylic acid ethyl ester

To a microwave vial was added intermediate 14.5 (200 mg), sodium azide (27 mg), zinc dibromide (84 mg). Water (2 ml) was added and the mixture was heated at 100° C. overnight. The mixture was evaporated off and the residue was purified by CC (DCM/MeOH 95/5) followed by preparative LC-MS (V).
LC-MS: $t_R$=0.91 min; [M+H]$^+$: 580.63.

The compounds of Examples 18 to 23 were prepared using a method analogous to that of the Example indicated between brackets, except that the last step of the corresponding Example was not carried out.

Example 18

4-((S)-4-tert-butoxycarbonyl-2-{[2-phenyl-6-(tetrahydro-pyran-4-yloxy)-pyrimidine-4-carbonyl]-amino}-butyryl)-piperazine-1-carboxylic acid ethyl ester

(Example 5). LC-MS: $t_R$=1.08 min; [M+H]$^+$: 626.54.

Example 19

4-((S)-4-tert-butoxycarbonyl-2-{[6-(1-methyl-piperidin-3-yloxy)-2-phenyl-pyrimidine-4-carbonyl]-amino}-butyryl)-piperazine-1-carboxylic acid ethyl ester

(Example 6). LC-MS: $t_R$=0.86 min; [M+H]$^+$: 639.59.

Example 20

4-((S)-2-{[6-(1-benzyl-piperidin-4-yloxy)-2-phenyl-pyrimidine-4-carbonyl]-amino}-4-tert-butoxycarbonyl-butyryl)-piperazine-1-carboxylic acid ethyl ester

(Example 7). LC-MS: $t_R$=0.90 min; [M+H]$^+$: 715.54.

Example 21

4-[(S)-3-(4-tert-butoxycarbonyl-phenyl)-2-({2-phenyl-6-[(tetrahydro-furan-3-yl)oxy]-pyrimidine-4-carbonyl}-amino)-propionyl]-piperazine-1-carboxylic acid ethyl ester

(Example 11). LC-MS: $t_R$=1.13 min; [M+H]$^+$: 674.70.

Example 22

((S)-4-tert-butoxycarbonyl-2-{[2-phenyl-6-(piperidin-4-yloxy)-pyrimidine-4-carbonyl]-amino}-butyryl)-piperazine-1-carboxylic acid ethyl ester

(Example 12). LC-MS: $t_R$=0.85 min; [M+H]$^+$: 625.54.

Example 23

4-((S)-4-tert-butoxycarbonyl-2-{[2-phenyl-6-(2,2,6,6-tetramethyl-piperidin-4-yloxy)-pyrimidine-4-carbonyl]-amino}-butyryl)-piperazine-1-carboxylic acid ethyl ester

(Example 13). LC-MS: $t_R$=0.90 min; [M+H]$^+$: 686.60.

Example 24

4-((S)-4-carboxy-2-{[6-(3-hydroxy-2-hydroxymethyl-propoxy)-2-phenyl-pyrimidine-4-carbonyl]-amino}-butyryl)-piperazine-1-carboxylic acid ethyl ester

24.1. (2,2-dimethyl-[1,3]dioxan-5-yl)-methanol

To a mixture of 2-hydroxymethylpropane-1,3-diol (200 mg) in THF (1 ml) was added 2,2-dimethoxypropane (0.278 ml) and p-toluenesulfonic acid monohydrate (11 mg). The mixture was stirred at RT for 4 h. NEt$_3$ (262 µl) was added and the mixture was stirred for further 15 min. The solvent was removed and the residue was purified by CC (DCM to DCM/MeOH 95/5) to afford 220 mg of the desired compound.
$^1$H-NMR (CDCl$_3$): 4.07 (d, 1H); 4.02 (d, 1H); 3.82 (d, 1H); 3.79 (m, 3H); 1.87 (m, 1H); 1.47 (s, 3H); 1.43 (s, 3H).

24.2. 4-((S)-4-tert-butoxycarbonyl-2-{[6-(2,2-dimethyl-[1,3]dioxan-5-ylmethoxy)-2-phenyl-pyrimidine-4-carbonyl]-amino}-butyryl)-piperazine-1-carboxylic acid ethyl ester This compound was prepared using a method analogous to that of Example 5, step 5.1, intermediate 24.1 replacing tetrahydro-2H-pyran-4-ol. The compound was however purified by CC (DCM to DCM/MeOH 8/2).
LC-MS: t$_R$=1.09; [M+H]$^+$: 670.51.

24.3. 4-((S)-4-carboxy-2-{[6-(3-hydroxy-2-hydroxymethyl-propoxy)-2-phenyl-pyrimidine-4-carbonyl]-amino}-butyryl)-piperazine-1-carboxylic acid ethyl ester This compound was prepared using a method analogous to that of Example 5, step 5.2, intermediate 24.2 replacing intermediate 5.1. The compound was however purified by CC (DCM/MeOH 8/2).
LC-MS: t$_R$=0.79 min; [M+H]$^+$: 574.43.

Example 25

4-((S)-4-carboxy-2-{[2-phenyl-6-(tetrahydro-thiopyran-4-yloxy)-pyrimidine-4-carbonyl]-amino}-butyryl)-piperazine-1-carboxylic acid ethyl ester 25.1. 4-((S)-4-tert-butoxycarbonyl-2-{[2-phenyl-6-(tetrahydro-thiopyran-4-yloxy)-pyrimidine-4-carbonyl]-amino}-butyryl)-piperazine-1-carboxylic acid ethyl ester This compound was prepared using a method analogous to that of Example 5, step 5.1, tetrahydro-2H-thiopyran-4-ol replacing tetrahydro-2H-pyran-4-ol and using DMF instead of THF. The compound was however purified by CC (EA/Hept 3/7).
LC-MS: t$_R$=1.13 min; [M+H]$^+$: 642.41.

25.2. 4-((S)-4-carboxy-2-{[2-phenyl-6-(tetrahydro-thiopyran-4-yloxy)-pyrimidine-4-carbonyl]-amino}-butyryl)-piperazine-1-carboxylic acid ethyl ester This compound was prepared using a method analogous to that of Example 5, step 5.2, intermediate 25.1 replacing intermediate 5.1. The compound was however purified by preparative LC-MS (IV).
LC-MS: t$_R$=0.99 min; [M+H]$^+$: 586.26.

Example 26

4-[(S)-4-carboxy-2-({2-phenyl-6-[(R)-(tetrahydrofuran-3-yl)oxy]-pyrimidine-4-carbonyl}-amino)-butyryl]-piperazine-1-carboxylic acid ethyl ester This compound was prepared using a method analogous to that of Example 1, step 1.8, (R)-(−)-3-hydroxytetrahydrofurane replacing 2-(2-methoxyethoxy)ethanol. The title compound was however purified by preparative LC-MS (III).
LC-MS: t$_R$=0.90 min; [M+H]$^+$: 556.28.

Example 27

4-[(S)-4-carboxy-2-({2-phenyl-6-[(S)-(tetrahydrofuran-3-yl)oxy]-pyrimidine-4-carbonyl}-amino)-butyryl]-piperazine-1-carboxylic acid ethyl ester 27.1. 4-((S)-4-tert-butoxycarbonyl-2-{[2-phenyl-6-(tetrahydro-thiopyran-4-yloxy)-pyrimidine-4-carbonyl]-amino}-butyryl)-piperazine-1-carboxylic acid ethyl ester This compound was prepared using a method analogous to that of Example 5, step 5.1, (S)-(+)-3-hydroxytetrahydrofurane replacing tetrahydro-2H-pyran-4-ol and using DMF instead of THF. The compound was however purified by CC (EA/Hept 3/7).
LC-MS: t$_R$=1.06 min; [M+H]$^+$: 612.39.

27.2. 4-[(S)-4-carboxy-2-({2-phenyl-6-[(S)-(tetrahydro-furan-3-yl)oxy]-pyrimidine-4-carbonyl}-amino)-butyryl]-piperazine-1-carboxylic acid ethyl ester This compound was prepared using a method analogous to that of Example 5, step 5.2, intermediate 27.1 replacing intermediate 5.1. The compound was however taken up in toluene and the solvent was evaporated off to remove residual TFA.
LC-MS: t$_R$=0.91 min; [M+H]$^+$: 556.40.

Example 28

4-[(S)-4-carboxy-2-({2-phenyl-6-[tetrahydro-furan-3-yloxy]-pyrimidine-4-carbonyl}-amino)-butyryl]-piperazine-1-carboxylic acid ethyl ester 28.1. 4-((S)-2-benzyloxycarbonylamino-3-tert-butoxycarbonyl-propionyl)-piperazine-1-carboxylic acid ethyl ester This compound was prepared using a method analogous to that of Example 1, step 1.1, Z-(L)-Asp(OtBu)—OH replacing Z-(L)-Asp(OtBu)—OH.
LC-MS: t$_R$=0.96 min; [M+H]$^+$: 464.36.

28.2. 4-((S)-2-amino-3-tert-butoxycarbonyl-propionyl)-piperazine-1-carboxylic acid ethyl ester This compound was prepared using a method analogous to that of Example 1, step 1.2, intermediate 28.1 replacing intermediate 1.1 and using EA instead of EtOH.
$^1$H-NMR (CDCl$_3$): 4.15 (q, 2H); 4.05 (dd, 1H); 3.6 to 3.4 (m, 8H); 2.6 (dd, 1H); 2.4 (dd, 1H); 1.6 (s, 2H); 1.45 (s, 9H); 1.25 (t, 3H).

28.3. 4-{(S)-3-tert-butoxycarbonyl-2-[(6-chloro-2-phenyl-pyrimidine-4-carbonyl)-amino]-propionyl}-piperazine-1-carboxylic acid ethyl ester This compound was prepared using a method analogous to that of Example 1, step 1.7, intermediate 28.2 replacing intermediate 1.2. The compound was however purified by CC (EA/Hept 3/7).
LC-MS: t$_R$=1.06 min; [M+H]$^+$: 546.42.

28.4. 4-[(S)-4-carboxy-2-({2-phenyl-6-[tetrahydro-furan-3-yloxy]-pyrimidine-4-carbonyl}-amino)-butyryl]-piperazine-1-carboxylic acid ethyl ester This compound was prepared using a method analogous to that of Example 1, step 1.8, intermediate 28.3 replacing intermediate 1.7 and 3-hydroxytetrahydrofurane replacing 2-(2-methoxyethoxy)ethanol. The compound was however purified by preparative CC (DCM/MeOH/AcOH 95/4.5/0.5).
LC-MS: $t_R$=0.88 min; [M+H]$^+$: 542.40.

Example 29

4-[(S)-4-carboxy-2-({2-phenyl-6-[tetrahydro-furan-3-yloxy]-pyrimidine-4-carbonyl}-amino)-butyryl]-piperazine-1-carboxylic acid butyl ester 29.1. 4-benzyl-piperazine-1-carboxylic acid butyl ester To a solution of 1-benzyl-piperazine (1.97 ml) and NEt$_3$ (1.9 ml) in DCM (100 ml) was added n-butyl chloroformate (1.47 ml). The mixture was stirred at RT for 2 h. Water was added, the org. phase separated, dried (Na$_2$SO$_4$) and evaporated off to give 3.13 g of a yellow oil.
LC-MS: $t_R$=0.73 min; [M+H]$^+$: 277.42.

29.2. Piperazine-1-carboxylic acid butyl ester

This compound was prepared using a method analogous to that of Example 1, step 1.2, intermediate 29.1 replacing intermediate 1.1.
LC-MS: $t_R$=0.54 min; [M+H+MeCN]$^+$: 226.39.

29.3. 4-((S)-2-benzyloxycarbonylamino-4-tert-butoxycarbonyl-butyryl)-piperazine-1-carboxylic acid butyl ester This compound was prepared using a method analogous to that of Example 1, step 1.1, intermediate 29.2 replacing 1-ethoxycarbonylpiperazine and using DCM instead of DCM/THF.
LC-MS: $t_R$=1.04 min; [M+H]$^+$: 506.49.

29.4. 4-((S)-2-amino-4-tert-butoxycarbonyl-butyryl)-piperazine-1-carboxylic acid butyl ester acetic acid salt This compound was prepared using a method analogous to that of Example 1, step 1.2, intermediate 29.3 replacing intermediate 1.1 and using EtOH/AcOH (100/1) instead of EtOH.
LC-MS: $t_R$=0.75 min; [M+H]$^+$: 372.49.

29.5. 4-{(S)-4-tert-butoxycarbonyl-2-[(6-chloro-2-phenyl-pyrimidine-4-carbonyl)-amino]-butyryl}-piperazine-1-carboxylic acid butyl ester This compound was prepared using a method analogous to that of Example 1, step 1.7, intermediate 29.4 replacing intermediate 1.2. The compound was however purified by CC (EA/Hept 3/7).
LC-MS: $t_R$=1.13 min; [M+H]$^+$: 588.49.

29.6. 4-[(S)-4-carboxy-2-({2-phenyl-6-[tetrahydro-furan-3-yloxy]-pyrimidine-4-carbonyl}-amino)-butyryl]-piperazine-1-carboxylic acid butyl ester This compound was prepared using a method analogous to that of Example 1, step 1.8, intermediate 29.5 replacing intermediate 1.7 and 3-hydroxytetrahydrofurane replacing 2-(2-methoxyethoxy)ethanol. The compound was however further processed as follows: water and DCM were added to the reaction mixture, TFA was added to the org. phase and after 1 h stirring, the solvents were removed. The residue was purified by preparative LC-MS (IV) to afford the desired compound.
LC-MS: $t_R$=0.97 min; [M+H]$^+$: 584.54.

Example 30

4-[(S)-4-carboxy-2-({2-phenyl-6-[(S)-(tetrahydro-furan-3-yl)oxy]-pyrimidine-4-carbonyl}-amino)-butyryl]-piperazine-1-carboxylic acid butyl ester 30.1. 4-[(S)-4-tert-butoxycarbonyl-2-({2-phenyl-6-[(S)-(tetrahydro-furan-3-yl)oxy]-pyrimidine-4-carbonyl}-amino)-butyryl]-piperazine-1-carboxylic acid butyl ester This compound was prepared using a method analogous to that of Example 5, step 5.1, intermediate 29.5 replacing intermediate 1.7, (S)-(+)-3-hydroxytetrahydrofurane replacing tetrahydro-2H-pyran-4-ol and using DMF instead of THF. The compound was however purified by CC (EA/Hept 2/8 to EA).
LC-MS: $t_R$=1.16 min; [M+H]$^+$: 639.50.

30.2. 4-[(S)-4-carboxy-2-({2-phenyl-6-[(S)-(tetrahydro-furan-3-yl)oxy]-pyrimidine-4-carbonyl}-amino)-butyryl]-piperazine-1-carboxylic acid butyl ester This compound was prepared using a method analogous to that of Example 5, step 5.2, intermediate 30.1 replacing intermediate 5.1. The compound was however purified by CC (EA to EA/MeOH 10/1).
LC-MS: $t_R$=1.03 min; [M+H]$^+$: 584.13.

Example 31

4-[(S)-4-carboxy-2-({2-phenyl-6-[(R)-(tetrahydro-furan-3-yl)oxy]-pyrimidine-4-carbonyl}-amino)-butyryl]-piperazine-1-carboxylic acid butyl ester This compound was prepared using a method analogous to that of Example 1, step 1.8, intermediate 29.5 replacing intermediate 1.7 and (R)-(−)-3-hydroxytetrahydrofurane replacing 2-(2-methoxyethoxy)ethanol. The compound was however purified by CC (EA/Hept 3/1, EA, EA/MeOH 9/1 then 7/3).
LC-MS: $t_R$=0.99 min; [M+H]$^+$: 584.29.

The compounds of Examples 32 to 35 were prepared using a method analogous to that of the Example indicated between brackets, except that the last step of the corresponding Example was not carried out.

Example 32

4-((S)-4-tert-butoxycarbonyl-2-{[6-(2,2-dimethyl-[1,3]dioxan-5-ylmethoxy)-2-phenyl-pyrimidine-4-carbonyl]-amino}-butyryl)-piperazine-1-carboxylic acid ethyl ester (Example 24). LC-MS: $t_R$=1.09; [M+H]$^+$: 670.51.

Example 33

4-((S)-4-tert-butoxycarbonyl-2-{[2-phenyl-6-(tetrahydro-thiopyran-4-yloxy)-pyrimidine-4-carbonyl]-amino}-butyryl)-piperazine-1-carboxylic acid ethyl ester (Example 25). LC-MS: $t_R$=1.13 min; [M+H]$^+$: 642.41.

Example 34

4-[(S)-4-tert-butoxycarbonyl-2-({2-phenyl-6-[(S)-(tetrahydro-furan-3-yl)oxy]-pyrimidine-4-carbonyl}-amino)-butyryl]-piperazine-1-carboxylic acid ethyl ester (Example 27). LC-MS: $t_R$=1.06 min; [M+H]$^+$: 612.39.

Example 35

4-[(S)-4-tert-butoxycarbonyl-2-({2-phenyl-6-[(S)-(tetrahydro-furan-3-yl)oxy]-pyrimidine-4-carbonyl}-amino)-butyryl]-piperazine-1-carboxylic acid butyl ester (Example 30). LC-MS: $t_R$=1.16 min; [M+H]$^+$: 639.50.

Example 36

4-[(S)-4-tert-butoxycarbonyl-2-({2-phenyl-6-[(R)-(tetrahydro-furan-3-yl)oxy]-pyrimidine-4-carbonyl}-amino)-butyryl]-piperazine-1-carboxylic acid butyl ester This compound was obtained as secondary product during the reaction performed for the synthesis of Example 31.
LC-MS (A): $t_R$=1.12 min; [M+H]$^+$: 640.37.

Example 37

4-((S)-4-carboxy-2-{[2-phenyl-6-(piperidin-4-yloxy)-pyrimidine-4-carbonyl]-amino}-butyryl)-piperazine-1-carboxylic acid butyl ester

37.1. 4-(2-{[6-(1-benzyl-piperidin-4-yloxy)-2-phenyl-pyrimidine-4-carbonyl]-amino}-(S)-4-tert-butoxycarbonyl-butyryl)-piperazine-1-carboxylic acid butyl ester This compound was prepared using a method analogous to that of Example 5, step 5.1, N-benzyl-4-hydroxypiperidine replacing tetrahydro-2H-pyran-4-ol and intermediate 29.5 replacing intermediate 1.7.
LC-MS (A): $t_R$=1.00 min; [M+H]$^+$: 743.09.

37.2. 4-((S)-4-tert-butoxycarbonyl-2-{[2-phenyl-6-(piperidin-4-yloxy)-pyrimidine-4-carbonyl]-amino}-butyryl)-piperazine-1-carboxylic acid butyl ester This compound was prepared using a method analogous to that of Example 1, step 1.2, intermediate 37.1 replacing intermediate 1.1 and using MeOH instead of EtOH.
LC-MS (A): $t_R$=0.94 min; [M+H]$^+$: 653.14.

37.3. 4-((S)-4-carboxy-2-{[2-phenyl-6-(piperidin-4-yloxy)-pyrimidine-4 carbonyl]-amino}-butyryl)-piperazine-1-carboxylic acid butyl ester This compound was prepared using a method analogous to that of Example 5, step 5.2, intermediate 37.2 replacing intermediate 5.1. The compound was however worked up as follows: the reaction mixture was evaporated off, the residue was taken up in EA and a Na$_2$CO$_3$ solution was added until pH 8; the phases were separated and the aq. phase was brought to pH 7 by adding a 1M HCl solution; upon addition of EA, the compound precipitated out and was filtered off and dried under HV.
LC-MS (A): $t_R$=0.84 min; [M+H]$^+$: 597.18.

Example 38

4-((S)-4-tert-butoxycarbonyl-2-{[2-phenyl-6-(piperidin-4-yloxy)-pyrimidine-4-carbonyl]-amino}-butyryl)-piperazine-1-carboxylic acid butyl ester This compound was prepared using a method analogous to that of Example 37, except that the last step was not carried out.
LC-MS (A): $t_R$=0.94 min; [M+H]$^+$: 653.14.

Biological Tests
P2Y$_{12}$ Receptor Binding Assay
Procedure

Chinese Hamster Ovary (CHO) cells with recombinant expression of the human P2Y$_{12}$ receptor were cultured in 24 well cell-culture plates. Cells were washed three times with binding buffer (50 mM Tris pH 7.4, 100 mM NaCl, 1 mM EDTA, 0.5% BSA). The cells were then incubated with 0.5 ml per well binding buffer containing tritium-labeled 2-methyl-thio-adenosine 5'-diphosphate (2-methyl-S-ADP) (between 100'000 and 300'000 dpm per well) and various concentrations of test compounds. After incubation at room temperature for 2 hours, cells were washed three times with binding buffer. Then, cells were solubilized by addition of 0.5 ml solubilization buffer (SDS, NaOH, EDTA). The content of each well was then transferred into beta-counter vials and 2.0 ml of Ultima Gold Scintillation liquid was added. After quantification of the cell-associated signal, extent of inhibition was calculated relative to maximal possible inhibition demonstrated by addition of excess of cold 2-methyl-S-ADP.

Results Obtained for the Compounds of Formula I

Using the procedure described above for the P2Y$_{12}$ receptor binding assay, IC$_{50}$s ranging from 12 nM to 1045 nM, with a mean value of about 190 nM, were measured for the compounds of the Examples 1 to 17, 24 to 31 and 37.

For example, the following results could be obtained for the Example compounds using the procedure described above for the P2Y$_{12}$ receptor binding assay:

| Example No. | IC$_{50}$ at P2Y$_{12}$ receptor binding assay (nM) |
| --- | --- |
| 1 | 108 |
| 6 | 238 |
| 10 | 126 |
| 17 | 94 |
| 37 | 71 |

Besides, the following additional results could be obtained for the Example compounds using the procedure described above for the P2Y$_{12}$ receptor binding assay:

| Example No. | IC$_{50}$ at P2Y$_{12}$ receptor binding assay (nM) |
| --- | --- |
| 36 | 448 |
| 38 | 13000 |

The invention claimed is:
1. A compound of formula I

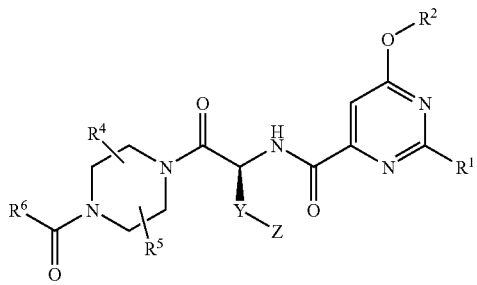

wherein
R¹ represents phenyl optionally substituted 1 to 3 times by substituents each independently selected from the group consisting of halogen, methyl, methoxy, trifluoromethyl and trifluoromethoxy;
R² represents an alkoxyalkoxyalkyl group, a dihydroxyalkyl group, a dimethoxyalkyl group or a (2,2-dimethyl-[1,3]dioxolan-4-yl)-alkyl group;
or R² represents a group of the formula

wherein
either m is 1 and n is 2 or 3, or m is 2 and n is 2; and
X represents O, S, NH, NR³, SO or SO₂;
R³ represents alkyl or arylalkyl;
or also R² represents 2,2,6,6-tetramethyl-piperidin-4-yl;
each of R⁴ and R⁵ represents independently hydrogen or methyl;
R⁶ represents alkoxy; and
Y represents alkylene or phenylalkylene, and Z represents —OH, —COOH, cyano, tetrazolyl or —COOR⁷, R⁷ representing alkyl;
or a salt of such a compound.
2. A compound according to claim 1, wherein R¹ represents phenyl optionally substituted once by halogen, methyl, methoxy, trifluoromethyl and trifluoromethoxy.
3. A compound according to claim 1, wherein R² represents an alkoxyalkoxyalkyl group, a dihydroxyalkyl group, a dimethoxyalkyl group or a (2,2-dimethyl-[1,3]dioxolan-4-yl)-alkyl group.
4. A compound according to claim 1, wherein R² represents group of the formula

or R² represents 2,2,6,6-tetramethyl-piperidin-4-yl.
5. A compound according to claim 1, wherein one of R⁴ and R⁵ represents hydrogen and the other represents hydrogen or methyl.
6. A compound according to claim 1, wherein Y represents alkylene or phenylalkylene, and Z represents —OH or —COOH or tetrazolyl.
7. A compound according to claim 6, wherein Y represents —CH₂—, —CH₂—CH₂— or —CH₂—CH₂—CH₂—, and Z represents —COOH.
8. A compound according to claim 1, which is selected from the group consisting of:
 4-[(S)-4-carboxy-2-({6-[2-(2-methoxy-ethoxy)-ethoxy]-2-phenyl-pyrimidine-4-carbonyl}-amino)-butyryl]-piperazine-1-carboxylic acid ethyl ester;
 4-((S)-4-carboxy-2-{[6-((R)-2,2-dimethyl-[1,3]dioxolan-4-ylmethoxy)-2-phenyl-pyrimidine-4-carbonyl]amino}-butyryl)-piperazine-1-carboxylic acid ethyl ester;
 4-((S)-4-carboxy-2-{[6-((S)-2,3-dihydroxy-propoxy)-2-phenyl-pyrimidine-4-carbonyl]-amino}-butyryl)-piperazine-1-carboxylic acid ethyl ester;
 4-((S)-4-carboxy-2-{[6-((R)-2,3-dimethoxy-propoxy)-2-phenyl-pyrimidine-4-carbonyl]-amino}-butyryl)-piperazine-1-carboxylic acid ethyl ester;
 4-((S)-4-carboxy-2-{[2-phenyl-6-(tetrahydro-pyran-4-yloxy)-pyrimidine-4-carbonyl]-amino}-butyryl)-piperazine-1-carboxylic acid ethyl ester;
 4-((S)-4-carboxy-2-{[6-(1-methyl-piperidin-3-yloxy)-2-phenyl-pyrimidine-4-carbonyl]-amino}-butyryl)-piperazine-1-carboxylic acid ethyl ester;
 4-((S)-2-{[6-(1-benzyl-piperidin-4-yloxy)-2-phenyl-pyrimidine-4-carbonyl]-amino}-4-carboxy-butyryl)-piperazine-1-carboxylic acid ethyl ester;
 4-((S)-4-carboxy-2-{[2-(4-fluoro-phenyl)-6-(tetrahydrofuran-3-yloxy)-pyrimidine-4-carbonyl]amino}-butyryl)-piperazine-1-carboxylic acid ethyl ester;
 ((S)-4-carboxy-2-{[6-(tetrahydro-furan-3-yloxy)-2-p-tolyl-pyrimidine-4-carbonyl]-amino}-butyryl)-piperazine-1-carboxylic acid ethyl ester;
 ((S)-4-carboxy-2-{[2-phenyl-6-(tetrahydro-furan-3-yloxy)-pyrimidine-4-carbonyl]-amino}-butyryl)-3-methyl-piperazine-1-carboxylic acid ethyl ester;
 4-[(S)-3-(4-carboxy-phenyl)-2-({2-phenyl-6-[(tetrahydro-furan-3-yl)oxy]-pyrimidine-4-carbonyl}-amino)-propionyl]-piperazine-1-carboxylic acid ethyl ester;
 4-((S)-4-carboxy-2-{[2-phenyl-6-(piperidin-4-yloxy)-pyrimidine-4-carbonyl]-amino}-butyryl)-piperazine-1-carboxylic acid ethyl ester;
 4-((S)-4-carboxy-2-{[2-phenyl-6-(2,2,6,6-tetramethyl-piperidin-4-yloxy)-pyrimidine-4-carbonyl]amino}-butyryl)-piperazine-1-carboxylic acid ethyl ester;
 4-[(S)-4-cyano-2-({2-phenyl-6-[(tetrahydro-furan-3-yl)oxy]-pyrimidine-4-carbonyl}-amino)-butyryl]-piperazine-1-carboxylic acid ethyl ester;
 4-((S)-4-carboxy-2-{[2-phenyl-6-(tetrahydro-furan-3-yloxy)-pyrimidine-4-carbonyl]-amino}-butyryl)-piperazine-1-carboxylic acid ethyl ester;
 4-[(S)-3-hydroxy-2-({2-phenyl-6-[(tetrahydro-furan-3-yl)oxy]-pyrimidine-4-carbonyl}-amino)-propionyl]-piperazine-1-carboxylic acid ethyl ester;
 4-[(S)-2-{[2-phenyl-6-(tetrahydro-furan-3-yloxy)-pyrimidine-4-carbonyl]-amino}-4-(1H-tetrazol-5-yl)-butyryl]-piperazine-1-carboxylic acid ethyl ester;
 4-((S)-4-tert-butoxycarbonyl-2-{[2-phenyl-6-(tetrahydropyran-4-yloxy)-pyrimidine-4-carbonyl]-amino}-butyryl)-piperazine-1-carboxylic acid ethyl ester;
 4-((S)-4-tert-butoxycarbonyl-2-{[6-(1-methyl-piperidin-3-yloxy)-2-phenyl-pyrimidine-4-carbonyl]-amino}-butyryl)-piperazine-1-carboxylic acid ethyl ester;
 4-((S)-2-{[6-(1-benzyl-piperidin-4-yloxy)-2-phenyl-pyrimidine-4-carbony]-amino}-4-tert-butoxycarbonyl-butyryl)-piperazine-1-carboxylic acid ethyl ester;

4-[(S)-3-(4-tert-butoxycarbonyl-phenyl)-2-({2-phenyl-6-[(tetrahydro-furan-3-yl)oxy]-pyrimidine-4-carbonyl}-amino)-propionyl]-piperazine-1-carboxylic acid ethyl ester;

((S)-4-tert-butoxycarbonyl-2-{[2-phenyl-6-(piperidin-4-yloxy)-pyrimidine-4-carbonyl]-amino}-butyryl)-piperazine-1-carboxylic acid ethyl ester;

4-((S)-4-tert-butoxycarbonyl-2-{[2-phenyl-6-(2,2,6,6-tetramethyl-piperidin-4-yloxy)-pyrimidine-4-carbonyl]-amino}-butyryl)-piperazine-1-carboxylic acid ethyl ester;

4-((S)-4-carboxy-2-{[6-(3-hydroxy-2-hydroxymethyl-propoxy)-2-phenyl-pyrimidine-4-carbonyl]-amino}-butyryl)-piperazine-1-carboxylic acid ethyl ester;

4-((S)-4-carboxy-2-{[2-phenyl-6-(tetrahydro-thiopyran-4-yloxy)-pyrimidine-4-carbonyl]-amino}-butyryl)-piperazine-1-carboxylic acid ethyl ester;

4-[(S)-4-carboxy-2-({2-phenyl-6-[(R)-(tetrahydro-furan-3-yl)oxy]-pyrimidine-4-carbonyl}-amino)-butyryl]-piperazine-1-carboxylic acid ethyl ester;

4-[(S)-4-carboxy-2-({2-phenyl-6-[(S)-(tetrahydro-furan-3-yl)oxy]-pyrimidine-4-carbonyl}-amino)-butyryl]-piperazine-1-carboxylic acid ethyl ester;

4-[(S)-4-carboxy-2-({2-phenyl-6-[tetrahydro-furan-3-yloxy]-pyrimidine-4-carbonyl}-amino)-butyryl]-piperazine-1-carboxylic acid ethyl ester;

4-[(S)-4-carboxy-2-({2-phenyl-6-[tetrahydro-furan-3-yloxy]-pyrimidine-4-carbonyl}-amino)-butyryl]-piperazine-1-carboxylic acid butyl ester;

4-[(S)-4-carboxy-2-({2-phenyl-6-[(S)-(tetrahydro-furan-3-yl)oxy]-pyrimidine-4-carbonyl}-amino)-butyryl]-piperazine-1-carboxylic acid butyl ester;

4-[(S)-4-carboxy-2-({2-phenyl-6-[(R)-(tetrahydro-furan-3-yl)oxy]-pyrimidine-4-carbonyl}-amino)-butyryl]-piperazine-4-carboxylic acid butyl ester;

4-((S)-4-tert-butoxycarbonyl-2-{[6-(2,2-dimethyl-[1,3]dioxan-5-ylmethoxy)-2-phenyl-pyrimidine-4-carbonyl]amino}-butyryl)-piperazine-1-carboxylic acid ethyl ester;

4-((S)-4-tert-butoxycarbonyl-2-{[2-phenyl-6-(tetrahydro-thiopyran-4-yloxy)-pyrimidine-4-carbonyl]-amino}-butyryl)-piperazine-1-carboxylic acid ethyl ester;

4-[(S)-4-tert-butoxycarbonyl-2-({2-phenyl-6-[(S)-(tetrahydro-furan-3-yl)oxy]-pyrimidine-4-carbonyl}-amino)-butyryl]-piperazine-1-carboxylic acid ethyl ester;

4-[(S)-4-tert-butoxycarbonyl-2-({2-phenyl-6-[(S)-(tetrahydro-furan-3-yl)oxy]-pyrimidine-4-carbonyl}-amino)-butyryl]-piperazine-1-carboxylic acid butyl ester;

4-[(S)-4-tert-butoxycarbonyl-2-({2-phenyl-6-[(R)-(tetrahydro-furan-3-yl)oxy]-pyrimidine-4-carbonyl}-amino)-butyryl]-piperazine-1-carboxylic acid butyl ester;

4-((S)-4-carboxy-2-{[2-phenyl-6-(piperidin-4-yloxy)-pyrimidine-4-carbonyl]-amino}-butyryl)-piperazine-1-carboxylic acid butyl ester; and 4-((S)-4-tert-butoxycarbonyl-2-{[2-phenyl-6-(piperidin-4-yl)oxy)-pyrimidine-4-carbonyl]amino}-butyryl)-piperazine-1-carboxylic acid butyl ester;

or a pharmaceutically acceptable salt of such a compound.

9. A compound according to claim 1, which is selected from the group consisting of:

4-[(S)-4-carboxy-2-({6-[2-(2-methoxy-ethoxy)-ethoxy]-2-phenyl-pyrimidine-4-carbonyl}-amino)-butyryl]-piperazine-1-carboxylic acid ethyl ester;

4-((S)-4-carboxy-2-{[6-((R)-2,2-dimethyl-[1,3]dioxolan-4-ylmethoxy)-2-phenyl-pyrimidine-4-carbonyl]-amino}-butyryl)-piperazine-1-carboxylic acid ethyl ester;

4-((S)-4-carboxy-2-{[6-((S)-2,3-dihydroxy-propoxy)-2-phenyl-pyrimidine-4-carbonyl]-amino}-butyryl)-piperazine-1-carboxylic acid ethyl ester;

4-((S)-4-carboxy-2-{[6-((R)-2,3-dimethoxy-propoxy)-2-phenyl-pyrimidine-4-carbonyl]-amino}-butyryl)-piperazine-1-carboxylic acid ethyl ester;

4-((S)-4-carboxy-2-{[2-phenyl-6-(tetrahydro-pyran-4-yloxy)-pyrimidine-4-carbonyl]-amino}-butyryl)-piperazine-1-carboxylic acid ethyl ester;

4-((S)-4-carboxy-2-{[6-(1-methyl-piperidin-3-yloxy)-2-phenyl-pyrimidine-4-carbonyl]-amino}-butyryl)-piperazine-1-carboxylic acid ethyl ester;

4-((S)-2-{[6-(1-benzyl-piperidin-4-yloxy)-2-phenyl-pyrimidine-4-carbonyl]-amino)-4-carboxy-butyryl}-piperazine-1-carboxylic acid ethyl ester;

4-((S)-4-carboxy-2-{[2-(4-fluoro-phenyl)-6-(tetrahydro-furan-3-yloxy)-pyrimidine-4-carbonyl]-amino}-butyryl)-piperazine-1-carboxylic acid ethyl ester;

((S)-4-carboxy-2-{[6-(tetrahydro-furan-3-yloxy)-2-p-tolyl-pyrimidine-4-carbonyl]-amino}-butyryl)-piperazine-1-carboxylic acid ethyl ester;

((S)-4-carboxy-2-{[2-phenyl-6-(tetrahydro-furan-3-yloxy)-pyrimidine-4-carbonyl]-amino}-butyryl)-3-methyl-piperazine-1-carboxylic acid ethyl ester;

4-[(S)-3-(4-carboxy-phenyl)-2-({2-phenyl-6-[(tetrahydro-furan-3-yl)oxy]-pyrimidine-4-carbonyl}-amino)-propionyl]piperazine-1-carboxylic acid ethyl ester;

4-((S)-4-carboxy-2-{[2-phenyl-6-(piperidin-4-yloxy)-pyrimidine-4-carbonyl]-amino}-butyryl)-piperazine-1-carboxylic acid ethyl ester;

4-((S)-4-carboxy-2-{[2-phenyl-6-(2,2,6,6-tetramethyl-piperidin-4-yloxy)-pyrimidine-4-carbonyl]amino}-butyryl)-piperazine-1-carboxylic acid ethyl ester;

4-[(S)-4-cyano-2-({2-phenyl-6-[(tetrahydro-furan-3-yl)oxy]-pyrimidine-4-carbonyl}-amino)-butyryl]-piperazine-1-carboxylic acid ethyl ester;

4-((S)-4-carboxy-2-{[2-phenyl-6-(tetrahydro-furan-3-yloxy)-pyrimidine-4-carbonyl]-amino}-butyryl)-piperazine-1-carboxylic acid ethyl ester;

4-[(S)-3-hydroxy-2-({2-phenyl-6-[(tetrahydro-furan-3-yl)oxy]-pyrimidine-4-carbonyl}-amino)-propionyl]-piperazine-1-carboxylic acid ethyl ester;

4-[(S)-2-{[2-phenyl-6-(tetrahydro-furan-3-yloxy)-pyrimidine-4-carbonyl]-amino}-4-(1H-tetrazol-5-yl)-butyryl]-piperazine-1-carboxylic acid ethyl ester;

4-((S)-4-tert-butoxycarbonyl-2-{[2-phenyl-6-(tetrahydro-pyran-4-yloxy)-pyrimidine-4-carbonyl]-amino}-butyryl)-piperazine-1-carboxylic acid ethyl ester;

4-((S)-4-tert-butoxycarbonyl-2-{[6-(1-methyl-piperidin-3-yloxy)-2-phenyl-pyrimidine-4-carbonyl]-amino}-butyryl)-piperazine-1-carboxylic acid ethyl ester;

4-((S)-2-{[6-(1-benzyl-piperidin-4-yloxy)-2-phenyl-pyrimidine-4-carbonyl]-amino}-4-tert-butoxycarbonyl-butyryl)-piperazine-1-carboxylic acid ethyl ester;

4-[(S)-3-(4-tert-butoxycarbonyl-phenyl)-2-({2-phenyl-6-[(tetrahydro-furan-3-yl)oxy]-pyrimidine-4-carbonyl}-amino)-propionyl]-piperazine-1-carboxylic acid ethyl ester;

((S)-4-tert-butoxycarbonyl-2-{[2-phenyl-6-(piperidin-4-yloxy)-pyrimidine-4-carbonyl]-amino}-butyryl)-piperazine-1-carboxylic acid ethyl ester; and 4-((S)-4-tert-butoxycarbonyl-2-{[2-phenyl-6-(2,2,6,6-tetramethyl-piperidin-4-yloxy)-pyrimidine-4-carbonyl]-amino}-butyryl)-piperazine-1-carboxylic acid ethyl ester;

or a pharmaceutically acceptable salt of such a compound.

10. The compound of claim 1 in the form of a pharmaceutically acceptable salt.

11. A pharmaceutical composition comprising at least one compound of claim 1, in free or a pharmaceutically acceptable salt thereof, and a pharmaceutically acceptable carrier, diluent or excipient.

12. A method for treating thrombosis, comprising administering to a patient in need thereof an effective amount of a compound according to claim 1, in free or a pharmaceutically acceptable salt form.

* * * * *